US011590006B2

United States Patent
Xiao et al.

(10) Patent No.: US 11,590,006 B2
(45) Date of Patent: Feb. 28, 2023

(54) SYSTEMS AND METHODS OF SOFT ROBOTIC ACTUATION WITH A LIQUID METAL ACTUATOR

(71) Applicant: The Regents of the University of Colorado, Denver, CO (US)

(72) Inventors: Jianliang Xiao, Louisville, CO (US); Zhanan Zou, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 16 days.

(21) Appl. No.: 17/097,758

(22) Filed: Nov. 13, 2020

(65) Prior Publication Data
US 2021/0205103 A1    Jul. 8, 2021

Related U.S. Application Data

(60) Provisional application No. 62/935,509, filed on Nov. 14, 2019.

(51) Int. Cl.
| | | |
|---|---|---|
| A61F 2/70 | (2006.01) | |
| B25J 15/08 | (2006.01) | |
| A61F 2/58 | (2006.01) | |
| B25J 9/00 | (2006.01) | |

(52) U.S. Cl.
CPC .......... *A61F 2/70* (2013.01); *A61F 2/586* (2013.01); *B25J 9/0015* (2013.01); *B25J 15/08* (2013.01)

(58) Field of Classification Search
CPC . A61F 2/70; A61F 2/586; B25J 9/0015; B25J 15/08
See application file for complete search history.

(56) References Cited

U.S. PATENT DOCUMENTS

| | | | |
|---|---|---|---|
| 5,741,884 A | 4/1998 | Cai et al. | |
| 2014/0314976 A1* | 10/2014 | Niiyama | G06F 3/0488 428/34.3 |
| 2015/0369264 A1* | 12/2015 | Felt | G01D 5/14 92/90 |

(Continued)

FOREIGN PATENT DOCUMENTS

| | | |
|---|---|---|
| JP | 2019019291 A | 2/2019 |
| WO | 2008062903 A1 | 5/2008 |

OTHER PUBLICATIONS

"Design and control of a robotic finger for prosthetic hands," in Proceedings 1999 IEEE/RSJ International Conference on Intelligent Robots and Systems. Human and Environment Friendly Robots with High Intelligence and Emotional Quotients, (Cat. No. 99CH36289), vol. 1, pp. vol. 1., 1999, 113-117.

(Continued)

*Primary Examiner* — Bruce E Snow
(74) *Attorney, Agent, or Firm* — Saul Ewing LLP; Kathryn Doyle; Domingos J. Silva

(57) ABSTRACT

Methods, systems, and methods of manufacture for soft robotic actuators are described herein. In one aspect, a soft robotic actuator can include an elastomeric material defining a cavity; a volume of liquid metal (LM) positioned within the cavity; and an energy source coupled to the LM, where the energy source is adapted or configured to alter a temperature of the volume of LM, whereby altering the temperature of the volume of LM initiates an actuation of the elastomeric material.

10 Claims, 17 Drawing Sheets

(56) References Cited

U.S. PATENT DOCUMENTS

2017/0349708 A1    12/2017   Sato et al.
2018/0143091 A1*   5/2018   Wood .................... G01L 1/2287
2022/0037581 A1*   2/2022   Tan .......................... C09D 4/06

OTHER PUBLICATIONS

"I-limb ultra | Touch Bionics." [Online]. Available: http://touchbionics.com/products/active-prostheses/i-limb-ultra. [Accessed: Feb. 24, 2019].
"Life changing myoelectric hand packed with the latest technology—bebionic." [Online]. Available: http://bebionic.com/the_hand. [Accessed: Feb. 24, 2019].
"International Search Report and Written Opinion dated Oct. 14, 2020 for International Appln. No. PCT/2020/36650".
"Michelangelo prosthetic hand." [Online]. Available: https://www.ottobockus.com/prosthetics/upper-limbprosthetics/solution-overview/michelangelo-prosthetic-hand/. [Accessed: Feb. 24, 2019].
"Vincent Systems GmbH." [Online]. Available: https://vincentsystems.de/en/. [Accessed: Feb. 24, 2019].
Andrianesis, et al., "Development and Control of a Multifunctional Prosthetic Hand with Shape Memory Alloy Actuators," J Intell Robot Syst, vol. 78, No. 2, May 2015, 257-289.
Belter, et al., "Performance characteristics of anthropomorphic prosthetic hands", IEEE, International Conference on Rehabilitation Robotics, 2011, pp. 1-7., 2011, 1-7.
Clement, et al., "Bionic prosthetic hands: A review of present technology and future aspirations", The Surgeon, vol. 9, No. 6, Dec. 2011, 336-340.
Controzzi, et al., "Design of Artificial Hands: A Review", The Human Hand as an Inspiration for Robot Hand Development, R. Balasubramanian and V. J. Santos, Eds. Cham: Springer International Publishing, 2014, 219-246.
Geethanjali, et al., "Myoelectric control of prosthetic hands: state-of-the-art review", Med Devices (Auckl), vol. 9,, Jul. 2016, 247-255.
Gerratt, et al., "Elastomeric Electronic Skin for Prosthetic Tactile Sensation," Advanced Functional Materials, vol. 25, No. 15, 2015, 2287-2295.
Le, et al., "A Novel Thermal-activated Shape Memory Penile Prosthesis: Comparative Mechanical Testing," Urology, vol. 99, pp. 136-141, Jan. 2017., Jan. 2017, 136-141.
Mehta, et al., "The Use of Dielectric Elastomer Actuators for Prosthetic, Orthotic and Bio-Robotic Applications,", Procedia Computer Science, vol. 133, Jan. 2018, 569-575.
Takeda, et al., ""Development of prosthetic arm with pneumatic prosthetic hand and tendon-driven wrist,"", Annual International Conference of the IEEE Engineering in Medicine and Biology Society, 2009, 5048-5051.
Yakacki, et al., "Tailorable and programmable liquidcrystalline elastomers using a two-stage thiol-acrylate reaction", RSC Advances, vol. 5, No. 25,, 2015, 18997-19001.
Yuan, et al., "3D printed reversible shape changing soft actuators assisted by liquid crystal elastomers", Soft Matter, vol. 13, No. 33, 2017, 5558-5568.
Bhinder, et al., "Flexion-Induced Automatic Prosthetic for Partial-Finger Amputees", Pacific, abstract only.
Schorger, et al., "Pneumatic hand prosthesis project", May 2018.
Zecca, et al., ""Control of Multifunctional Prosthetic Hands by Processing the Electromyographic Signal," CRB, vol. 30, No. 4-6", 2002.

\* cited by examiner

A

B

C

D

SYSTEMS AND METHODS OF SOFT ROBOTIC ACTUATION WITH A LIQUID METAL ACTUATOR

CROSS-REFERENCE TO RELATED APPLICATION

This application claims the benefit of priority under 35 U.S.C. § 119(e) to U.S. Provisional Patent Application Ser. No. 62/935,509, filed Nov. 14, 2019. The entire content of this application is hereby incorporated by reference herein.

BACKGROUND OF THE INVENTION

Liquid Crystal Elastomers (LCEs) exhibit similar actuation behavior to natural muscle due to their dramatic contraction, reversible deformation, response to multiple stimuli, and great potential for micro-scale robotics. Combining liquid crystal orientation and cross-linked polymer networks, LCEs have attracted much attention towards creating artificial muscles. Mechanical alignment is the most widely used actuation option due to its convenience and ease of operation, offering the most potential for LCE actuators to mimic the large, linear actuation of natural muscle tissues. However, mechanical actuation includes significant drawbacks. For example, mechanical actuation can be heavy, particularly in relation to the material that is being actuated. Further, mechanical actuation is limited in its range of motion and degrades over time.

There is thus a need in the art for novel actuation systems that mimic natural muscle. The present invention addresses and meets this need.

SUMMARY OF THE INVENTION

One aspect of the invention provides a soft robotic actuator, including an elastomeric material defining a cavity; a volume of liquid metal (LM) positioned within the cavity; and an energy source coupled to the LM, wherein the energy source is adapted or configured to alter a temperature of the volume of LM, whereby altering the temperature of the volume of LM initiates an actuation of the elastomeric material.

This aspect can include a variety of embodiments. In one embodiment, the altered temperature of the volume of LM can cause a phase transition of the elastomeric material, where the actuation is initiated by the phase transition. In another embodiment, the cavity can be further defined by a very high bonding (VHB) film coupled to the elastomeric material. In another embodiment, the actuation occurs according to a direction of alignment of the elastomeric material. In another embodiment, the actuation can include a shrinking, a twisting, or a bending of the elastomeric material.

In another embodiment, the volume of LM can include a gallium compound. In another embodiment, the elastomeric material can include liquid crystal elastomer (LCE), Polydimethylsiloxane (PDMS), a silicone rubber, or a combination thereof. In another embodiment, the soft robotic actuator can further include a temperature-activated pigment either painted onto or mixed into the elastomeric material.

In another aspect, a method of manufacturing the soft robotic actuator can include layering the volume of LM onto a base layer according to a predefined pattern; casting a volume of elastomeric material onto the volume of LM and the base layer; and curing the volume of elastomeric material for a predefined period of time and at a predefined temperature.

In one embodiment, the method can further include generating a direction of alignment for actuation of the soft robotic actuator, where the generating comprises straining and UV treating the soft robotic actuator subsequent to the curing. In some cases, the straining can include a uniaxial strain, and where the actuation includes a shrinking, a twisting or a bending of the soft robotic actuator. In some cases, the straining can include a biaxial strain, and where the actuation includes a shrinking, a twisting or a bending of the soft robotic actuator.

Another aspect of the invention includes a self-sensible soft robotic actuator, including a soft robotic actuator, another section of elastomeric material defining another cavity; an LM sensor including another volume of LM positioned within the other cavity; and a base layer including a first surface and a second surface, where the first surface is coupled to the soft robotic actuator and the second surface is coupled to both the other volume of LM and the other section of elastomeric material.

In one embodiment, the self-sensible robotic actuator can include a data collector coupled to the LM sensor, wherein the data collector is adapted or configured to receive data corresponding to a change in resistance of the LM sensor; determine, from the change in resistance, a change in strain on the LM sensor; and identify from the change in strain on the LM sensor an actuation of the self-sensible soft robotic actuator.

In another aspect, a method of actuating a soft robotic actuator can include generating an energy current via the energy source; altering the temperature of the volume of LM from an energy current originating from the energy source; and actuating the soft robotic actuator through a transference of thermal energy from the volume of LM to the elastomeric material.

In one embodiment, the actuating can include the soft robotic actuator transitioning from a resting mode to an active mode. In one embodiment, the method can further include terminating the energy current, where the soft robotic actuator returns to the resting mode from the active mode subsequent to the termination. In one embodiment, the active mode can further include a contraction, a bend, or a twist of the soft robotic actuator.

In one embodiment, the method can further include forming a discontinuity within the volume of LM; increasing the temperature of the soft robotic actuator; and repairing the discontinuity by the increase in temperature.

In one aspect, a soft robotic prosthetic can include at least one finger prosthetic having a length, a proximal end, and a distal end, where the at least one finger prosthetic includes a flexible structure configured to bend radially along the length of the prosthetic finger; a soft robotic actuator, where the soft robotic actuator is positioned along the length of the at least one finger prosthetic; a plurality of pulleys coupling the soft robotic actuator to the finger prosthetic, where the at least one finger prosthetic bends when an energy current is generated by the energy source; and a base coupled to the proximal end of the at least one finger prosthetic.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

Figure 1:
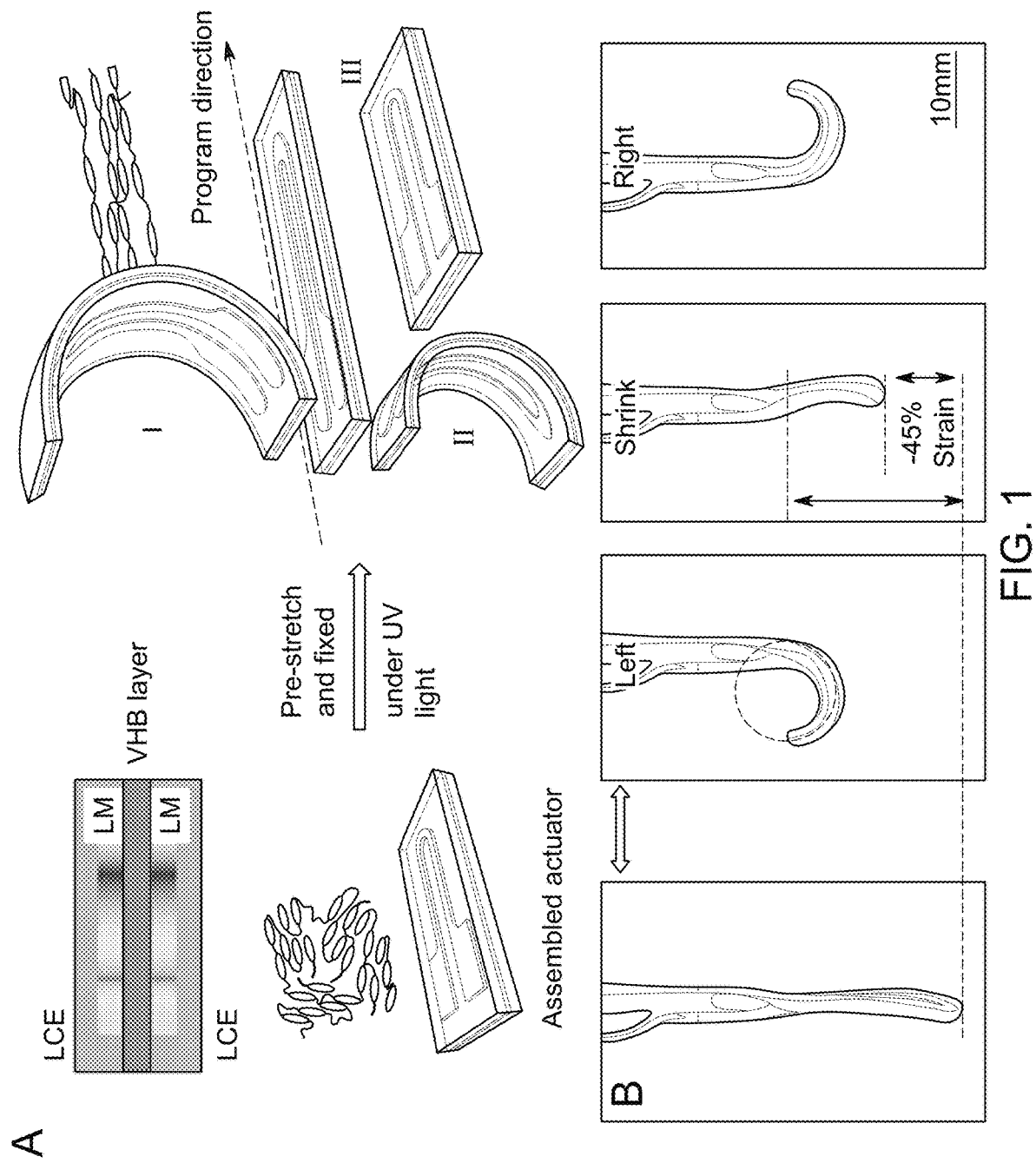
FIG. 1 illustrates conceptual demonstrations and experimental results of Liquid Crystal Elastomer (LCE)/Liquid Metal (LM) artificial muscles (LLAMs), according to embodiments of the claimed invention. Panel (A) illustrates a conceptual design about the LCE/LM actuator. LM was patterned on each side of a Very High Bond (VHB) layer and encapsulated with liquid LCE. After a 1st stage of polymerization, the LCE/LM actuator was pre-stretched and further polymerized under UV light. The actuator can perform bending and/or shrinking. Panel (B) depicts experimental images of the LCE/LM actuator, which can bend and shrink. The actuator can obtain a shrinking strain of up to 45%.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Soft Robotic Actuator

The claimed invention includes novel systems, methods, and methods of manufacture for soft robotic actuators. These soft robotic actuators include a volume of liquid metal (LM) embedded within an elastomeric material. When the LM receives an energy current, such as an electrical current supplied from a voltage source, the temperature of the LM can increase. A thermal exchange can occur between the LM and the elastomeric material, causing the elastomeric material to shrink, bend, and/or twist, according to an alignment direction of the elastomeric material. A soft robotic actuator can therefore actuate based on the LM's change in temperature.

The use of LM for actuation has several benefits over current robotic actuation methods. For example, the use of LM reduces the volume and weight requirements for actuating the robot, particularly when compared to conventional DC motors that are implemented in robotics. Another benefit to the use of LM is its durability and resiliency. The examples discussed below illustrate that even during a multitude of testing cycles, the soft robots incorporating the LM actuator do not display signs of significant degradation, which is an issue with conventional mechanical motors. Further, even when the LM actuator is somehow disturbed, (e.g., the LM becomes solidified, broken and the like), the self-healing properties of the LM can allow for the channel to be repaired without user interference (e.g., in the above example, increasing the temperature of the LM). Yet another aspect is the range of possible motion provided by the LM actuator. As the LM actuator is not confined by the mechanical limitations of conventional motors, the soft robot can experience a wider range of motion and increased strain compared to conventional robotics.

Elastomeric Material

The soft robotic actuator can include an elastomeric material. The elastomeric material can include a polymer composition with high viscosity and elasticity characteristics, which can allow for a high degree of movement and resilience. For example, the elastomeric material can include a liquid crystal elastomer (LCE), Polydimethylsiloxane (PDMS), or a composition manufactured by Ecoflex® (e.g., Ecoflex 00-30, etc.). In some cases, the composition can vary between portions (e.g., film layers) of the soft robotic actuator. For example, a first layer of elastomeric material can be composed of LCE, while a second layer of elastomeric material can be composed of PDMS, which can be bonded on top of the first layer, under the first layer, etc.

Liquid Metal

The soft robotic actuator can also include a volume of LM. The LM can include any metallic composition that includes a relatively low melting point (e.g., at or near room temperature). In the below examples, gallium is used as the LM. Further, some examples of gallium alloys that can be the LM can include gallium-indium (EGaIn), gallium-indium-tin (Galistan), gallium-tin-zinc (Ga—Sn—Zn), gallium-zinc (Ga—Zn), gallium-tin (Ga—Sn), and gallium-aluminum (Ga—Al). However, other LMs such as gallium alloys, rubidium, francium, mercury, and cesium can be used, for example.

Energy Source

The soft robotic actuator can also include an energy source. The energy source can be coupled to the LM, and can generate and transmit to the LM an energy current. While the below examples discuss the energy source as a voltage source and the energy current as an electrical current, other energy sources such as a current source, a thermal energy source, and the like, can be used as the energy source.

Base Layer

The soft robotic actuator can also include a base layer. The base layer can provide structural integrity to the soft robotic layer. For example, the LM can be layered (e.g., stenciled) onto the base layer in some cases, and the elastomeric material layered over the base layer and the LM. Further, the base layer can provide a bonding composition for the elastomeric material and/or the LM. In some cases, the base layer can be a very high bonding (VHB) film. VHB film can include an adhesive with high performance bonding characteristics, such as high performance acrylic, multi-purpose acrylic, silicone, cyanoacrylate, and the like.

Soft Robot Fabrication

Fabricating the soft robot can include curing the elastomeric material to a preferred shape. Prior to curing, the elastomeric material can be moldable or manipulated to alter its shape. In some cases, the elastomeric material can be shaped to form a cavity, where the cavity is subsequently used as the LM housing or channel. In other cases, the elastomeric material can be shaped to couple to a base layer.

In the case of using a base layer, the LM can first be patterned onto the base layer prior to coupling the elastomeric material. The elastomeric material can then be coupled (e.g., layered) onto the base layer/LM combination. Subsequently, the elastomeric material can be cured. Curing can involve a predefined increased temperature (80°, 100°, 120°, 140°, 200° F., etc.) over a predefined period of time (e.g., 1, 4, 10, 15, 20 hours, etc.). After curing, the elastomeric material can include a cured, resting shape, while also possessing a wide range of motion. During this fabrication process, the energy source can be coupled to the LM. In the case of a voltage source, electrical leads can be inserted into the LM and coupled to the voltage source to create a circuit.

The fabrication process can include multiple layering processes. For example, a soft robotic actuator can include multiple layers of elastomeric material, where each can include its own curing stage. Further, in some cases, multiple volumes of LM can be patterned on or contained within multiple cavities or channels (e.g., which can be used for bending or twisting movements, etc.). In some cases, a base layer can include LM volumes on multiple surfaces, which are each encapsulated by elastomeric material.

Straining the Soft Robotic Actuator

The soft robotic actuator can be strained to form a direction of alignment. The straining can include the physical manipulation of the elastomeric material (e.g., after curing). For example, the elastomeric material can be stretched, twisted, bent, compacted, and the like. The straining can generate a reversible chain formation in the elastomeric material (e.g., the direction of alignment). A change in temperature of the elastomeric material can lead to deformation of the elastomeric material according to the direction of alignment.

Actuation

Actuation of the soft robotic actuator occurs by altering the temperature of the elastomeric material to generate the deformation discussed above. Energy can be passed to the LM, which can increase the temperature of the LM. As the LM increases in temperature, thermal energy can be passed to the elastomeric material, subsequently increasing the temperature of the elastomeric material. The increase in temperature of the elastomeric material can result in a physical deformation of the elastomeric material along a direction of alignment.

Further, a decrease in temperature of the elastomeric material can also actuate the soft robotic actuator. For example, after deformation, the energy source can be turned off, which can lead to the temperature of the LM decreasing. This can result in a decrease of the temperature of the elastomeric material. As the temperature decreases, the elastomeric material can return to its original positioning (e.g., pre-deformation).

This actuation can be harnessed in a multitude of ways. Discussed below include embodiments of a soft robotic walker, a soft robotic prosthetic (e.g., a soft robotic hand), a camouflageable soft robotic actuator, along with twisting, bending, shrinking, etc., actuators.

EXAMPLES

The invention is now described with reference to the following Examples. These Examples are provided for the purpose of illustration only, and the invention is not limited to these Examples, but rather encompasses all variations that are evident as a result of the teachings provided herein.

Experimental Setup 1

Camouflaging, a well-known phenomenon in nature, is widely adopted by animals and plants. Enabling soft robots to blend into their surroundings, however, is not as easy as those naturally-selected creatures make it seem. The main challenges include reversibly mapping designed flat structures into complex 3D topologies and triggering localized texture changes, similar to a muscular hydrostat. A biomimetic artificial muscle could be the key to solving this problem. Liquid Crystal Elastomers have proven to be one of the artificial materials most like natural muscle. Moreover, precise controlling and down-scaling of the artificial muscles remains challenging. In our work, we successfully invented an artificial muscle with Liquid Crystal Elastomer as the actuation material and LM (Gallium) elements as the controlling units. A self-sensible soft robot capable of crawling and camouflaging into its background was fabricated based on our novel artificial muscles.

Introduction

For naturally selected animals and plants, camouflage is a basic skill to survive every day. Big cats with stripes and dots hide in the bushes waiting to ambush, chameleons blend into colorful tree branches, and octopus change their skin textures to mimic anything from a sea rock to sea plants. However, helping soft robots blend into their surroundings remains a challenge. In nature, animals have dedicated muscle system for supporting such functions. Pneumatic actuation of soft silicone materials is successfully introduced to develop a camouflageable skin.

Biological muscle contracts under stimulation, and thus interacts with its surrounding tissues. Localized and miniature pattern control is efficiently realized on such a platform. Liquid Crystal Elastomers (LCEs) exhibit the most similar actuation behavior to natural muscle, due to their dramatic contraction, reversible deformation, response to multiple stimuli, and great potential for micro-scale robotics. Combining liquid crystal orientation and cross-linked polymer networks, LCEs have attracted much attention towards creating artificial muscles. The reversible change in chain formation due to a shift in temperature leads to macroscopic deformation. Alignment prior to actuation is critical for LCE actuators. Various methods have been considered including taking advantage of diamagnetic and dielectric anisotropy of mesogens, which is limited to certain monomers and requires large magnetic fields. Surface patterning, achieved by such means as rubbing with a cloth, is adopted as well, but limited to thin membranes (<100 um). Mechanical alignment is the most widely used option due to its convenience and ease of operation, offering the most potential for LCE actuators to mimic the large, linear actuation of natural muscle tissues. Stimulating the aligned LCEs also remains a challenge. Introducing a dye into the LCE network to enable a response to light proves to be a good method, but is confined to certain formulas and difficult for precise unit controlling. In other cases, heaters were adhered to the surface of aligned LCE layers [Yu kai paper, soft matter] to trigger phase disorder of the aligned LCE sheet, but this method was limited to small local strain and bending deformation. Embedding heaters into the LCE material could efficiently enhance the heat transferring from the heaters to the LCE network and enable linear actuation closer to natural muscle tissues. Unfortunately, conventional heaters based on solid metal and composite materials could be damaged under large alignment strain (up to 600%). A Liquid Metal (LM), however, could handle such deformation without issue, and is especially suitable for LCE alignment. Further, LM heaters would introduce almost no extra confinements to the active polymer network, owning to their fluidic properties above a certain temperature. LM, at the same time, has been proved to work as very sensitive strain sensors. A self-sensible actuator thus can be achieved on such system.

In this work, we choose an LCE network based on a two-stage thiol-acrylate reaction, and embed patterned LM heater (99.99% Gallium) directly into the LCE network. The LM heater deforms with the LCE network during alignment with no damage. Linear actuation, bending, and twisting are realized with this system. Gallium (melting at 30° C.) was chosen as the material for the LM heater and patterned using stencil methods. The LM heater not only remains robust during actuation but also does not confine the deformation of LCE networks. Large linear strains over 100% can be realized, which is much higher than natural muscle. Inspired by biological tissue, passive and active materials are then combined as a system, mimicking dramatically changing surface patterns. Taking advantage of the sensing capability of LM heaters, a self-sensible soft walker is also realized.

We embedded the LM (Gallium) into an LCE network to mimic the performance of natural muscular tissues. The LCE/LM artificial muscles (LLAMs) were fabricated layer by layer, as shown conceptually in FIG. 1A and FIG. 6A. The LM heaters (250 um thick) were patterned on top of a 3M VHB layer (25 um thick) utilizing stencil methods. The very high bond (VHB) layer was used as an adhesion medium and could thus firmly hold the LM heater patterns. The thin layer of VHB only slightly affects actuation due to its much thinner thickness. We achieved a low characteristic cross-section aspect ratio for the LM heaters (~2:1, shown in FIG. 7A) to avoid the collapse of fluidic channels when the system undergoes large deformations. A liquid LCE layer (500 um thick) was then cast on top of the LM heater patterns and allowed to cure at 80° C. for 24 hours. After the first stage of cross-linking, the LCE layer adhered to the VHB surface and LM heaters very well and formed a liquid channel. The sandwiched structure was then stretched with 100% uniaxial strain and further cross-linked under UV light (365 nm wavelength) for 15 minutes. In the first example (FIG. 1A), we fabricated a LLAM with a length of 20 mm, a thickness of 2.4 mm and a width of 5 mm. Two LM heaters were embedded on each side of the VHB layer. When a current (3 A-5 A) goes through either one of the heaters, the LLAM bends toward that side. With current running through both heaters, the LLAM shrinks, as shown in FIG. 1A I, II, and III, on the right. Both bending and linear actuation can thus be achieved on a single actuator using simple patterns, as shown in experimental FIG. 1B. We measured a smallest bending radius of about 5 mm, and a linear contraction strain of about 45%, which is much higher than that of biological muscle and other forms of soft actuators. It should be noted that the optimal linear actuation strain can be further enhanced if a larger pre-stretch is introduced during alignment.

Figure 6:
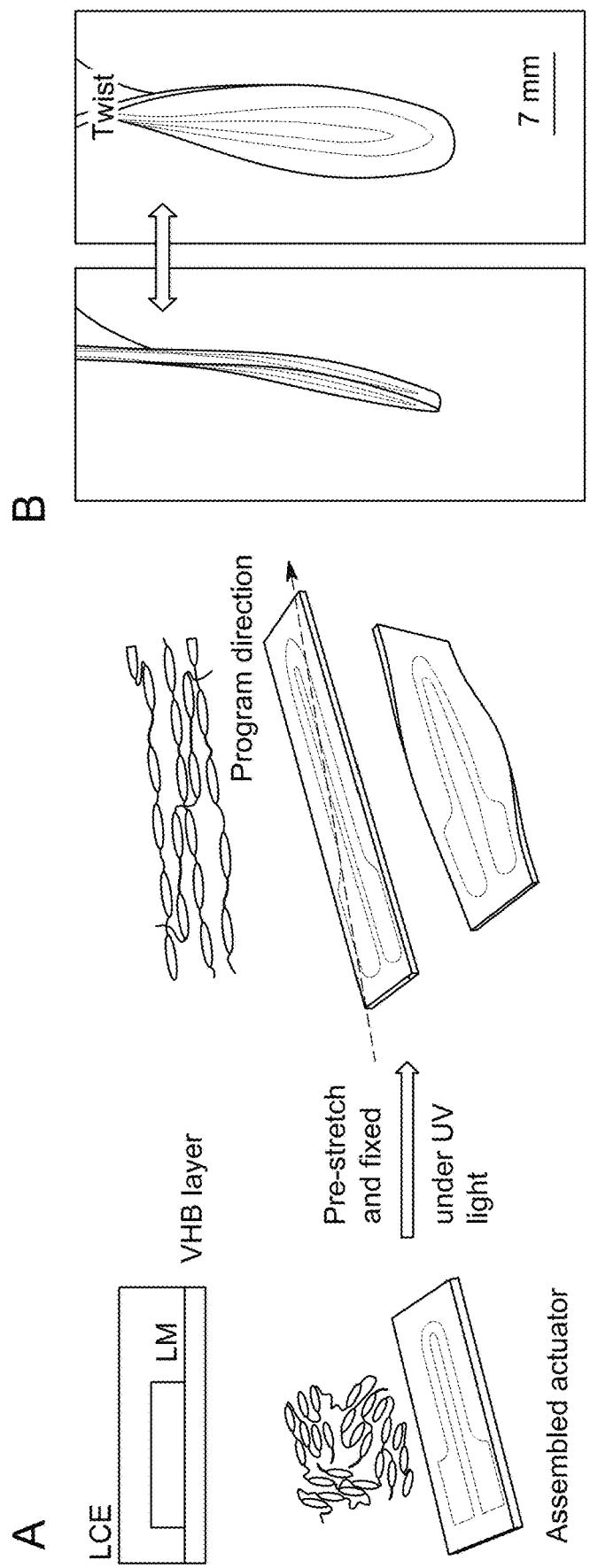
FIG. 6 depicts a twisting deformation of an LLAM, according to an embodiment of the claimed invention.

For a second example, a simpler actuator (with a length of 20 mm, a thickness of 1.2 mm and a width of 5 mm) was fabricated using only one LM heater embedded in the LCE network. The alignment direction was slightly biased, as shown in FIG. 6A. The LLAM primarily twisted when the LM heater was engaged, with a twisting angle of over 900, comparable to other means but based on a simpler design, shown in FIG. 6B. The twisting deformation occurred due to a bias alignment and thermal gradient within the LCE/LM composite layer, easily realized on our platform.

Figure 7:
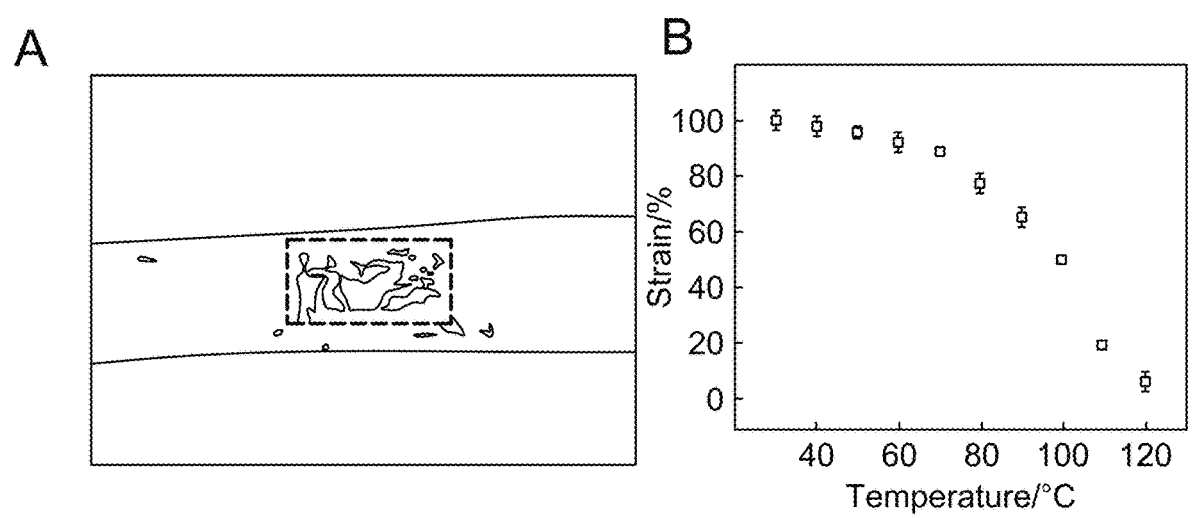
FIG. 7 depicts an LM channel cross-section (Panel (A)) a strain-to-temperature relationship of LCE actuators (Panel (B)), according to embodiments of the claimed invention.

A mechanical analysis of the LM heater channel and a thermal analysis of the LLAM were carried out, as shown in FIG. 2A and FIG. 2B, respectively. Compared to a solid metal, LM can undergo 'infinite' deformation without damage. In the LLAM, the LM heater deformed along with the fluidic channel during alignment (FIG. 2A, middle), experiencing 69% to 96% strain, indicated in FIG. 2A, right. Solid metals, on the other hand, cannot withstand such deformation during LCE alignment. In the case of our LLAM, localized temperature distribution dominates the deformation. To better understand this mechanism, a thermal analysis (steady state heat transfer analysis) was performed to reveal the temperature distribution on both the surface and throughout a cross-section of the LLAM, shown in FIG. 2B. The surface temperature distribution (FIG. 2B, middle) was first compared to a thermal image taken with an infrared camera (FIG. 2B, left). We then investigated the thermal distribution of a cross-section, as in FIG. 2B, right. When one of the heaters was on, the temperature of the LCE layer beside this heater was much higher than on the other side: ~110° C. versus ~70° C. To our knowledge, the LCE network deforms gradually with respect to temperature, as shown in FIG. 7B. Bending thus dominates due to the unsymmetrical actuation strains of the two LCE layers with different temperatures. When both heaters were on, the thermal distribution was symmetrical and more uniform along the cross-section, leading to linear actuation.

Another advantage of introducing the LM heater into an LCE network is the self-healing property of the LM itself. In our work, the LM heater cross-section was designed with a small aspect ratio, thus damage almost never happened due to actuation. However, to investigate the self-healing of our LLAM, we first cooled the LLAM to lower than LM melting temperature (~15° C.) and manually broke it, shown in FIG. 2C, left. By simply heating up the LLAM, the gallium heater was healed, shown in FIG. 2C, right. The electrical conductivity of the Gallium heater during 10 cycles of breaking and self-healing is shown in FIG. 2D.

Since the LLAMs response to electric stimulation depends on time and current intensity, a detailed characterization of the bending, shrinking and twisting performance of the LLAM was carried out, as shown from FIG. 2E to FIG. 2J. Five different current values were applied and the actuation performances were recorded with respect to time. FIG. 2E shows the radius change of the LLAM with respect to time and applied current. When a current was imposed on one of the LM heaters, the bending radius of the LLAM decreased with time and was relatively stable after about 5 seconds. In fact, higher current leads to a smaller stable bending radius and a faster actuation speed. Similar phenomena were observed for linear shrinking and twisting, as shown in FIG. 2F and FIG. 2G. We also investigated the performance of LLAM after many cycles. The cycle tests for bending, shrinking and twisting actuations were repeated at least 100 times each at a current of 5 A and duration of 5 s, which offered the maximum actuation power. For bending and twisting cycle tests, currents were applied for 5 seconds. For the shrinking cycle test, the current was run for 10 s, due to the effect's slower response. The cycle tests data are shown in FIG. 2G-FIG. 2I. After cycling through 100 times, the actuators show almost no change in performance.

Figure 3:
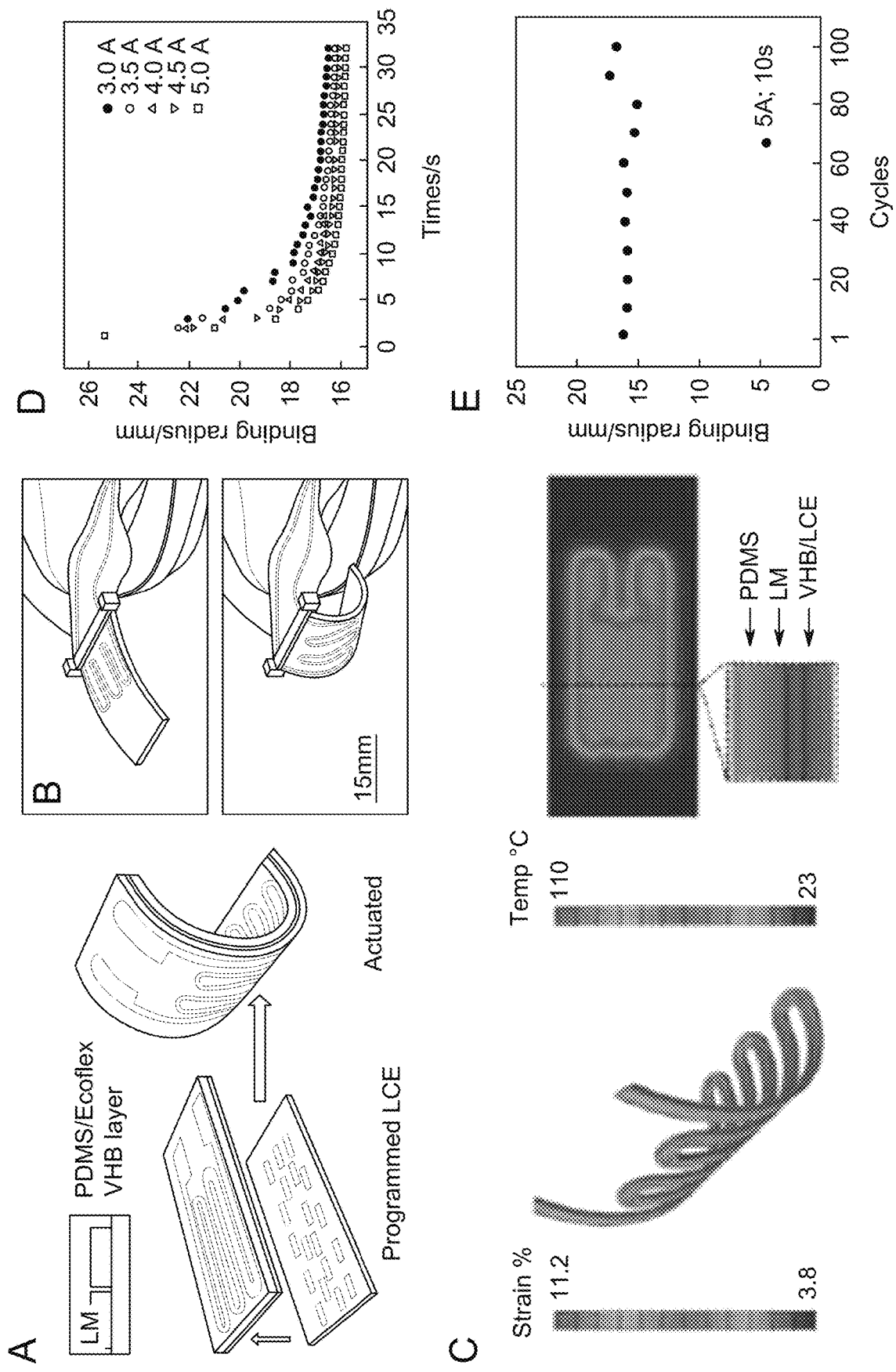
FIG. 3 illustrates designs and testing of active/passive artificial tissue (APAT), according to embodiments of the claimed invention. Panel (A) conceptualizes the APAT. LM was casted by passive materials like PDMS or Ecoflex, and a programmed piece of LCE layer was attached underneath. The LM heater can heat the LCE layer and the actuator subsequently bends. Panel (B) depicts an experimental image of the APAT. Panel (C) depicts FEA analysis of the strain and temperature distribution of the LM channel. Panels (D,E) illustrate characterizations of the APAT bending performance, and cycle testing of 100 times. Panels (F-H) depict designed pattern transformations of the APAT. The alignment direction offers different patterns and can function as a single unit. Multiple units of LCE layers can deform a 2D plate piece into more complex 3D geometry.
Figure 3:
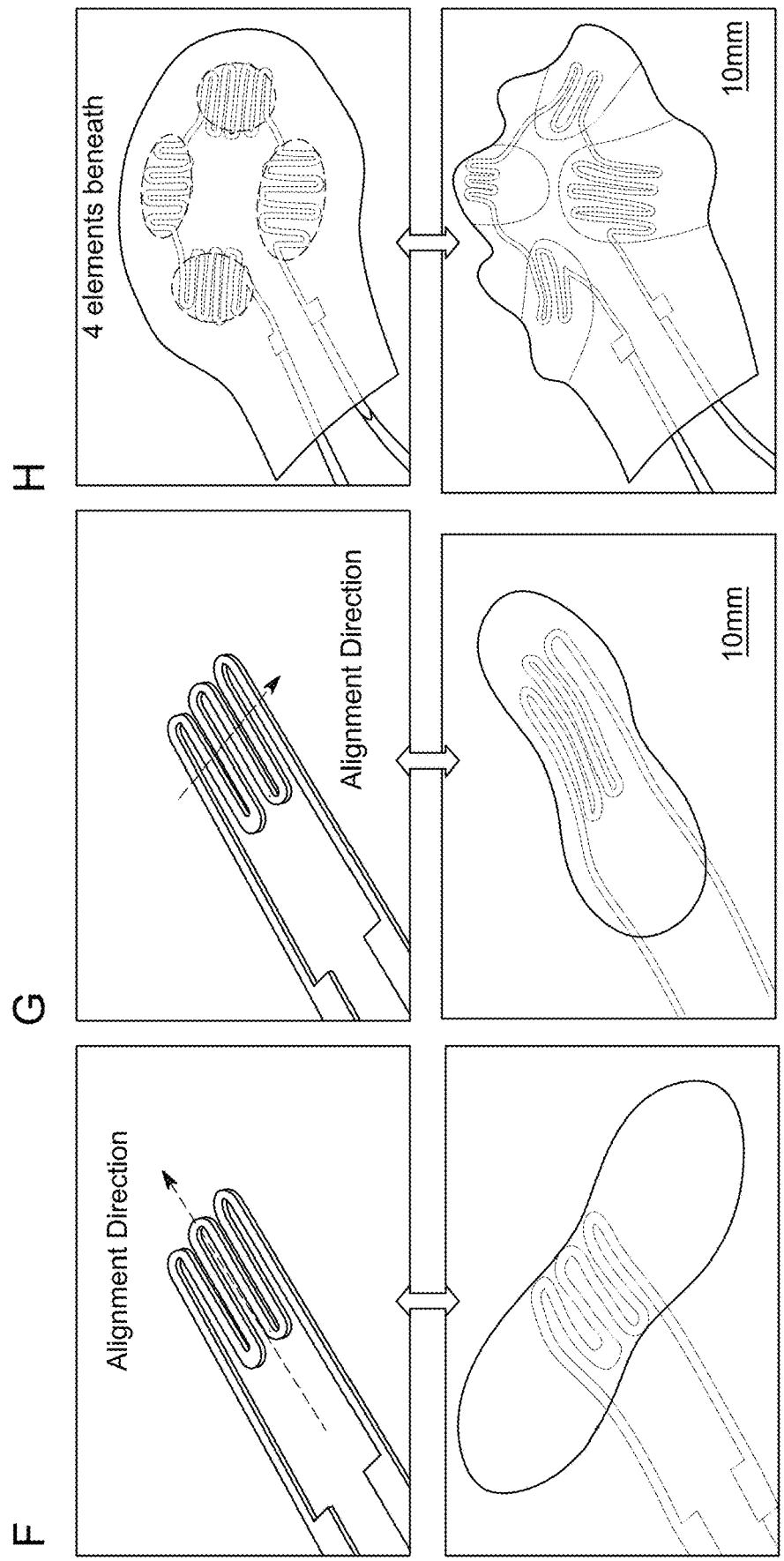

Natural muscular tissues, especially for cephalopods, consist of active muscles and passive surrounding tissues and skins. The combination of such active/passive systems paves the way for large actuation, complex texture transformations, and overall surface topology shifting. We integrated our active LLAM with passive soft materials such as PDMS (Polydimethylsiloxane) and Ecoflex (Ecoflex-00-30), and achieved the transformation from a 2D surface to a targeted, complex 3D shape. We created an active/passive artificial tissue (APAT), as indicated in FIG. 3A. The APAT consists mainly of two parts: the LM heater micro channel, and the aligned LCE unit. We fabricated the LM heater channel with a similar method to that mentioned before but replaced the LCE with PDMS or Ecoflex. An LCE layer was prepared separately and aligned as a sheet beneath the LM heater channel. Patterns were then cut out of the LCE sheet using a mechanical cutter and the LCE layer was adhered to the LM channel on the VHB side directly. The adhesion between VHB and LCE layers proved to be very robust. Such a combination enables a soft, bio-mimicking actuator with both active 'muscle' and passive 'tissue.' The deformation, in this case, is mainly bending, as shown in FIG. 3B. Upon heating, the aligned LCE layer shrinks while the passive layer remains almost unchanged, with the strain mismatch of the two layers leading to bending deformation, as indicated in FIG. 3B, bottom. Both mechanical and thermal analyses are demonstrated in FIG. 3C, with the mechanical analysis of LM fluidic channel deformation highlighting the advantage of adopting LM as heater material. Evidently, the maximum strain is about 10% (FIG. 3C, left), which is higher than the yielding strain of most metals. Thermal analysis shows the thermal distribution of the cross-section of our APAT, shown in FIG. 3C, right.

The bending performance of our APAT was characterized as shown in FIG. 3D. Five current values (3 A, 3.5 A, 4 A, 4.5 A, and 5 A) are supplied, lasting for 30 s, and the final bending radius of each case was recorded. Experimental data indicates that the bending radius increases with time and becomes stable after about 10 s, with higher current values leading to smaller stable bending radii and quicker actuation. To investigate the robustness of our APAT, tests of 100 cycles were performed. A current of 5 A applied for 10 seconds was applied to the LM heater and the bending radius at 10 seconds was recorded, as shown in FIG. 3E. Cycle test data (100 times) reveals that the APAT shows almost no obvious performance change.

To further demonstrate the combined actuation of active and passive soft materials, a programmed LCE layer with an ellipse shape was attached under a much larger sheet of Ecoflex with an embedded LM heater. The LM heater patterns covered the LCE layer from beneath and a current of 5 A was applied to trigger deformation. Localized bulging formed due to the LCE layer shrinking, deforming the passive surrounding materials, as shown in FIG. 3F and FIG. 3G. In detail, we aligned the ellipse LCE layer as indicated by the purple dashed lines in FIG. 3F and FIG. 3G. More complex deformations can be realized with more independent elements. Here, four LCE elements were attached under the Ecoflex layer, each with a custom-designed LM heater on top. A current of 5 A was applied to all the heaters, stimulating all four LCE elements at the same time. The overall actuation of the LCE elements thus deformed the flat 2D surface into a complex 3D configuration, as shown in FIG. 3H. The pictures also indicate an advantage of LM heaters, especially in this case, as the LM heaters are not only robust, but they do not confine the actuation. Finite element analysis was used to predict the mapping of any 2D surface into a complex 3D topology, as shown from FIG. 8A to FIG. 8D.

Figure 4:
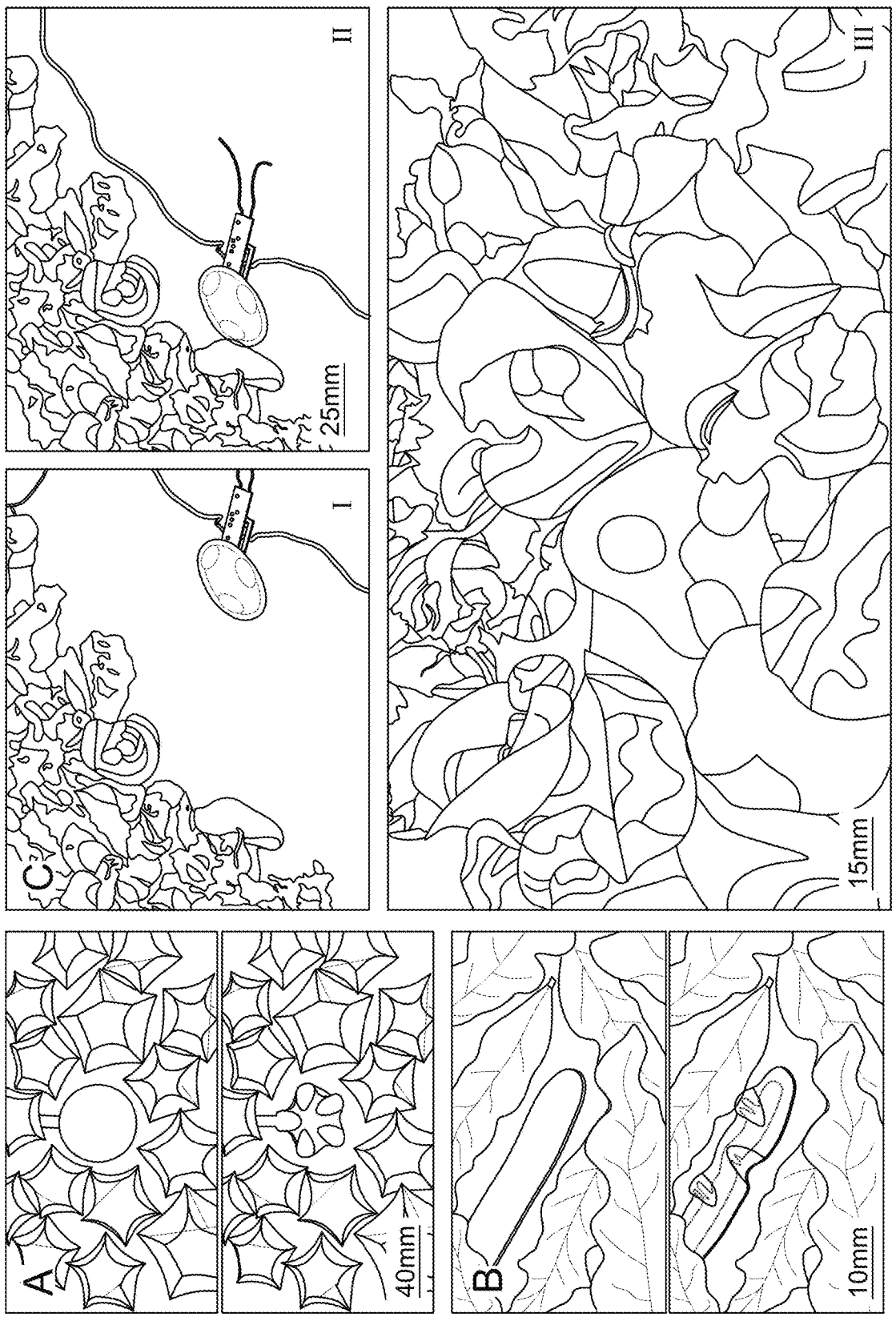
FIG. 4 depicts a soft robot with a camouflageable skin, according to embodiments of the claimed invention. Panel (A) depicts experimental images showing a flat piece of APAT deformed into a sea star shape when a voltage of 5 A was applied to the LM heaters. Panel (B) depicts experimental images displaying a flat APAT stripe that can be deformed into a water plant shape and change its surface color when current is applied to the APAT. The shape change is due to the actuation of APAT while the color change is due to a ThermoChromic pigment mixed inside the polymer network, which changed its color at temperature higher than 30 degree Celsius. Panel (C) illustrates a soft robot than can move forward into a Fungi group as well as deform its back layer skin into a similar shape. The soft walker was composed of APAT, which bended during heating and flattened when voltage decreased. Uni-friction feet were embedded beneath to enable the soft robot to move forward.

In nature, mollusks tout the most potential for deformation. A leech can elongate its body to more than 5 times its original length, a snail can retract into a tiny shell with limited space, and an octopus can blend into its surroundings almost perfectly. Those creatures achieve complex shape change due to muscular hydrostat, which requires incompressible muscle actuation. Inspired by nature, a camouflaging soft robot was developed using the APAT approach with FIG. 4 demonstrating three different kinds of camouflage systems. FIG. 4A shows the deformation of a flat surface into a star like structure when electricity is connected to the LM heaters. The shape can be held for as long as the current is supplied. Assorted sizes of origami stars—made by hand—were placed around the APAT to compare the shape. The star camouflage was realized by attaching four LCE elements beneath an Ecoflex sphere sheet. LM heaters were fabricated in certain areas where the LCE elements were attached. The stimulation and dissimulation of the LCE elements led to the reversible shape transformation from a 2D circular surface into a 3D star shape. Pink pigment was painted on both the APAT circle sheet and origami stars. FIG. 4B shows an APAT stripe camouflaged into a cluster of water plant leaves. The APAT stripe was painted with a ThermoChromic Temperature Activated Pigment, which is blue at room temperature and shifts to green at temperatures higher than 30° C. (FIG. 4B). Higher temperature further triggered the transformation of the APAT from a flat stripe into a shape similar to that of the surrounding water plant leaves, shown in FIG. 4B, bottom.

Next, a soft robot with camouflageable (camo) skin is demonstrated in FIG. 4C: I, II and III. The camo soft robot was composed of two parts: a soft walker on the bottom and a camo skin on top. The walker was fabricated into a rectangular APAT stripe with three fishing hooks beneath to function as uni-frictional feet with the capability to move forward with simple bending and recovery. The camo skin consisting of three LCE elements was bonded to the soft walker using a drop of liquid Ecoflex that was subsequently cured. As demonstrated in FIG. 4C I and II, the soft robot traveled from an empty area into a group of real fungi. The skin, painted with a black pigment, was triggered to display the camo effect, simultaneously deforming the robot into the shape of its surroundings. The position of the fungus group in FIG. 4C III was arranged for the best camo effect.

Figure 5:
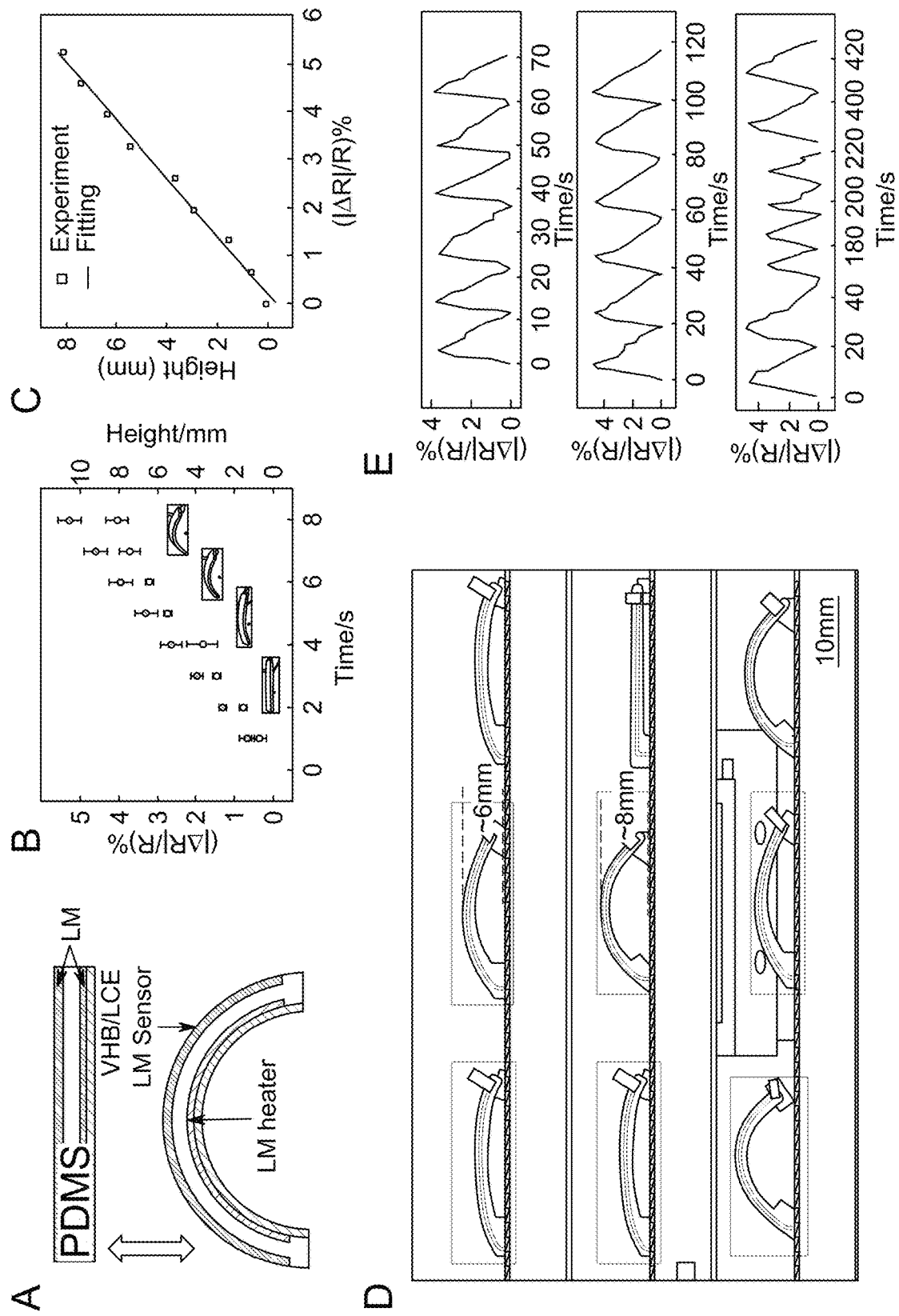
FIG. 5 depicts an LM/LCE, self-sensing soft walker, according to embodiments of the claimed invention. Panel (A) depicts an image illustrating how the LCE soft walker senses its own movement. An LM heater was embedded close to the LCE layer for actuation, and an LM sensor was fabricated into the top layer that senses strain during deformation. Panel (B) depicts a graph showing the relationship of the LM sensor resistance change and the soft walker bending arch (height) over time, after electrical current was applied to the LM heater. Panel (C) depicts the relationship of the arch height with the LM sensor resistance change. Panel (D) depicts experimental images showing the soft walker: moving forward with different amplitude (6 mm high and 8 mm high); and squeezing into narrow space. The surface is made into uni-frictional for better controlling of each step of moving. Panel (E) depicts how the soft walker can sense its own moving corresponding to three different case: moving with low amplitude; moving with high amplitude; squeezing into narrow space and move out.

The soft walker, at the same time, can be self-sensible, since LM can be used to fabricate very sensitive strain sensors. A self-sensible soft walker that senses its own deformation during work has been carried out with APAT. FIG. 5A indicates the design and principle of such self-sensible soft walker. Two LM structures were fabricated on both sides of the PDMS encapsulation layers. A programed LCE layer was attached to one side working as the actuator. When actuating, the soft walker bended, leading to an increase of strain of the LM sensor on the other side, the deformation further led to the increase of resistance which was recorded by a data collector (National instrumental NI USB-9162). Thus, the deformation of the soft walker can be mapped to the resistance change of the LM sensor, as indicated in FIG. 5B. The height of the bending walk and the resistance change of the sensor are recorded with respect to time. Thus we obtained a relationship of the deformation with the resistance change, shown in FIG. 5C. Noted here that the resistance change could also be from the heating effect from the LM heater on the other side. To further investigate this problem, a comparison experiment was carried out, in which the soft walker was fixed at two ends and was applied the same actuation current, shown in FIG. 9B. The resistance change of the LM sensor was recorded in FIG. 9D, almost no obvious resistance change was observed for the comparison experiment, thus, exclude the influence of heat. Further, thermal analysis (transient heat transfer analysis) of the temperature change of the LM sensor was also carried out shown in FIG. 9F. At time of 1 s, 2 s, 3 s, 4 s and 5 s, the temperature of the LM sensor shows no obvious change, this is due to the low thermal conductivity of the PDMS layer and its comparatively large thickness (2 mm).

The soft walker can sense its amplitude of moving as indicated in FIG. 5D. A current of 3.5 A was applied to the LM heater for ~4 seconds and cut off, the walk accomplished a cycle of motion and got one step forward, repeating such process ended up in moving from right to left, shown in FIG. 5D, upper. The corresponding resistance change of the walker during moving was recorded as well in FIG. 5E, upper. Similar processes but with a longer heating time were used to let the walker have a larger moving amplitude, and the resistance change was also recorded, shown in FIG. 5D, middle and FIG. 5E, middle. Further, the soft walker was allowed to move at different amplitude and pass through a narrow space, shown in FIG. 5D, bottom, with a corresponding resistance change recorded. The experiments indicates that the APAT system can function well as both actuators and sensors.

Comments

In this work, LM and LCE were combined to create a novel, completely soft actuation system. LCE offers advantages over all kinds of soft actuators and requires only heat stimulation. By introducing the LM heater, much more robust actuation can be achieved. The LCE heater, at the same time, is self-healable. A clever heating element pattern design helps to avoid the collapse of the LM fluidic channel. Inspired by natural muscle and tissue, active and passive soft materials were then joined to achieve complex deformation and camouflage abilities. In current research, the patterning of LM is limited to stenciling methods. Thus, to realize a small aspect ratio in the LM fluidic channel, the LM heater was made thick and bulky. In the future, other methods can be introduced to pattern much smaller scale LM heaters, which could further enhance the robustness and lower the current input for tomorrow's soft robots.

Materials Preparation

The LCE was prepared using a two-stage thiol-acrylate Michael addition-photopolymerization (TAMAP) reaction. 4-bis-[4-(3-acryloyloxypropypropyloxy) benzoyloxy]-2-methylbenzene (RM257), pentaerythritol tetrakis(3-mercaptopropionate) (PETMP), 2,2-(ethylenedioxy) diethanethiol (EDDET), (2-hydroxyethoxy)-2-methylpropiophenone (HHMP) and dipropylamine (DPA) were used as received from Sigma Aldrich, except for RM257, which was from Wilshire Technologies. 4 g of RM257, 0.217 g of PETMP, 0.9157 g of EDDET and 0.0257 g of HHMP were dissolved into 1.6 g of toluene solution. 0.568 g of DPA (diluted with toluene at a ratio of 1:50) was then added into the solution for the first stage polymerization and cured at 80° C. for 12 h. The cured polymer was then stretched and exposed to UV light for at least 15 mins (Omincure 2000) to trigger the second stage of polymerization.

Fabricating LM Patterns

The LM patterns were fabricated using a simple stencil method. Card stock paper (thickness, 350 um) was purchased from Amazon and cut into the designed pattern with a laser cutter. The paper mask was then placed on top of a VHB layer (3M VHB). LM was then cast on top of the mask, with the sticky surface of the VHB holding the LM pattern very well. After patterning, the paper mask was removed, leaving the LM pattern on top of the VHB layer. Copper wires were connected to the LM pattern as electrical connections, and experiments reveal that simple contact between the LM and copper guarantees robust electrical connectivity.

Embedding LM into LCE, Ecoflex, or PDMS

To embed LM into other materials, the LM patterns were fabricated using the aforementioned method. The LCE solution remained in liquid state for around 15 mins after adding diluted DPA. The solution is cast on top of the LM patterns and placed in a vacuum chamber for 1 minute at 508 mmHg in order to remove any air bubbles caused by mixing. Everything was then sandwiched between two glass slices and cured at 80° C. for 12 h. When programming, LCE/LM system is heated above 30° C., then stretched and exposed to UV light with the LCE side on top. For PDMS and Ecoflex, the LM pattern was simply cast, degassed, and cured in the same way. Programmed LCE layers were then attached to the other side of the VHB. Due to the sticky nature of VHB, the adhesion between the VHB and LCE proved to be very reliable.

Fabricating Camouflageable Soft Robot

The camo soft robot consists of two parts: the soft walker and the camo skin. Both parts were fabricated with the same system of passive/active component combination. To enable the walker to move forward, fishing hooks were partly embedded into the two ends of the walker, all pointed backwards. A current was applied to the heater in the walker to trigger bending and then cut off to recover, the repetition of which enables the walker to move forward. The camo skin was fabricated with an Ecoflex sheet and three LCE elements and adhered to the top of the walker with liquid Ecoflex.

Testing Bending, Shrinking, and Twisting

To test the actuation performance of the devices, five current values were supplied, ranging from 3.5 A to 5 A. The actuation effects were recorded by video and the bending radius, strain, and twisting angle were analyzed directly from the video cut. For the cycle test, a current of 5 A was applied to the bending and twisting case of LLAM for 5 seconds, and a current of 5 A and was applied to linear shrinking of LLAM and bending of APAT for 5 seconds.

Self-Sensible Soft Walker

The self-sensible soft walker was fabricated using the same methods mentioned previously, a uni-friction surface was made on top of which the soft walker can move forward.

Chemicals and Polymerization of LCE

The LCE was prepared using a two-stage thiol-acrylate Michael addition-photopolymerization (TAMAP) reaction. 4-bis-[4-(3-acryloyloxypropypropyloxy) benzoyloxy]-2-methylbenzene (RM257), pentaerythritol tetrakis(3-mercaptopropionate) (PETMP), 2,2-(ethylenedioxy) diethanethiol (EDDET), (2-hydroxyethoxy)-2-methylpropiophenone (HHMP) and dipropylamine (DPA) were used as received from Sigma Aldrich, except for RM257, which was from Wilshire Technologies.

4 g of RM257, 0.217 g of PETMP, 0.9157 g of EDDET and 0.0257 g of HHMP were dissolved into 1.6 g of toluene solution. The solution was heated up to 80° C. to let the RM257 powder dissolved into toluene, and mixed with the other monomers by a mechanical vortex shaker. After cooling down to room temperature, 0.568 g of DPA (diluted with toluene at a ratio of 1:50) was then added into the solution for the first stage polymerization, the mixed solution was degassed with a vacuum chamber until the gas disappears, the clear solution was then casted on glass plate and cured at 80° C. for 12 h. Toluene evaporated during this process.

The cured polymer was then stretched and exposed to UV light for at least 15 mins (Omincure 2000) to trigger the second stage of polymerization, and programmed to be an actuator.

Fabrication of LCE/LM Actuators

The LCE/LM actuators were fabricated with stencil method and casting method. A silicone coated thick paper (~150 um, Amazon) was used to fabricate the pattern mask with a laser cutter (Pinty Laser Cutter). The mask was then attached to a layer of VHB tape (3M@VHB), LM droplets was casted on top and everything were then sandwiched between two clean glass slides. The pattern on the mask was transferred to the LM. After removing the residues and paper mask, the LM pattern was on top of the VHB tape. Then the liquid LCE mixed with DPA was casted on top of the LM pattern, and degassed until no bubbles remained. Then another clean glass was put on top of the liquid LCE with a spacer of ~1 mm. The samples were put in an oven at 80° C. for 24 h until the first cross-link stage was fully completed.

The cured LCE/LM composite was then pre-stretched under 100% strain, and exposed under UV light for 15 mins with the LCE side on top. Thus the LCE/LM actuator was fabricated. To make a shrinkable and bendable actuator, two such actuators were attached together with another side of the VHB tape, thus having two LM heaters on each side. Heating any side of the heater will lead to the bending toward that side, and shrinking if both heaters are on. For the twisting actuator, the same method was adopted except the programming stage. Instead of applying a uniaxial strain, a biaxial strain was applied during programming, shown in FIG. 6A. Heating will result in a twisting and bending motion in general.

Fabrication of LCE/Ecoflex/LM Artificial Muscle

The artificial muscle in this work is based on a combination of active part LCE and passive part Ecoflex or PDMS. The PDMS was used for fabricating soft walkers, and Ecoflex was used for fabricating camouflageable skin. The goal to adopting such design and combination is for more precise controlling and easier fabrication. Similar patterning method was used as described in the previous section, then liquid PDMS or Ecoflex was casted on top of the pattern and VHB tape and degassed until no bubbles remained. Same glass slides and spacers were used to control the thickness of the PDMS or Ecoflex layer. After curing at 80° C. for 1 h, a programmed LCE layer with a thickness of 150 um was attached to the other side of the VHB tape. When the LM patterns are heated up the LCE layer will also be quickly heated up due to the low thickness of both VHB tape and LCE layer.

Finite Element Analysis for Predicting 3D Mapping from 2D Designs

Both mechanical and thermal analyses were carried out for a better understanding of the APATs and LLAMs. Commercial software ABAQUS was used for the simulation. C3D8R element was used to simulate the LCE, LM channel, and passive materials like PDMS or Ecoflex. The modulus of the LCE is 2 MPa, PDMS is 3 MPa, Ecoflex is 60 kPa. Since the LM in the working condition is liquid, we model it with a much smaller modulus of 1 Pa. The bonding between each different materials are set as perfect bonding for simplification.

Figure 8:
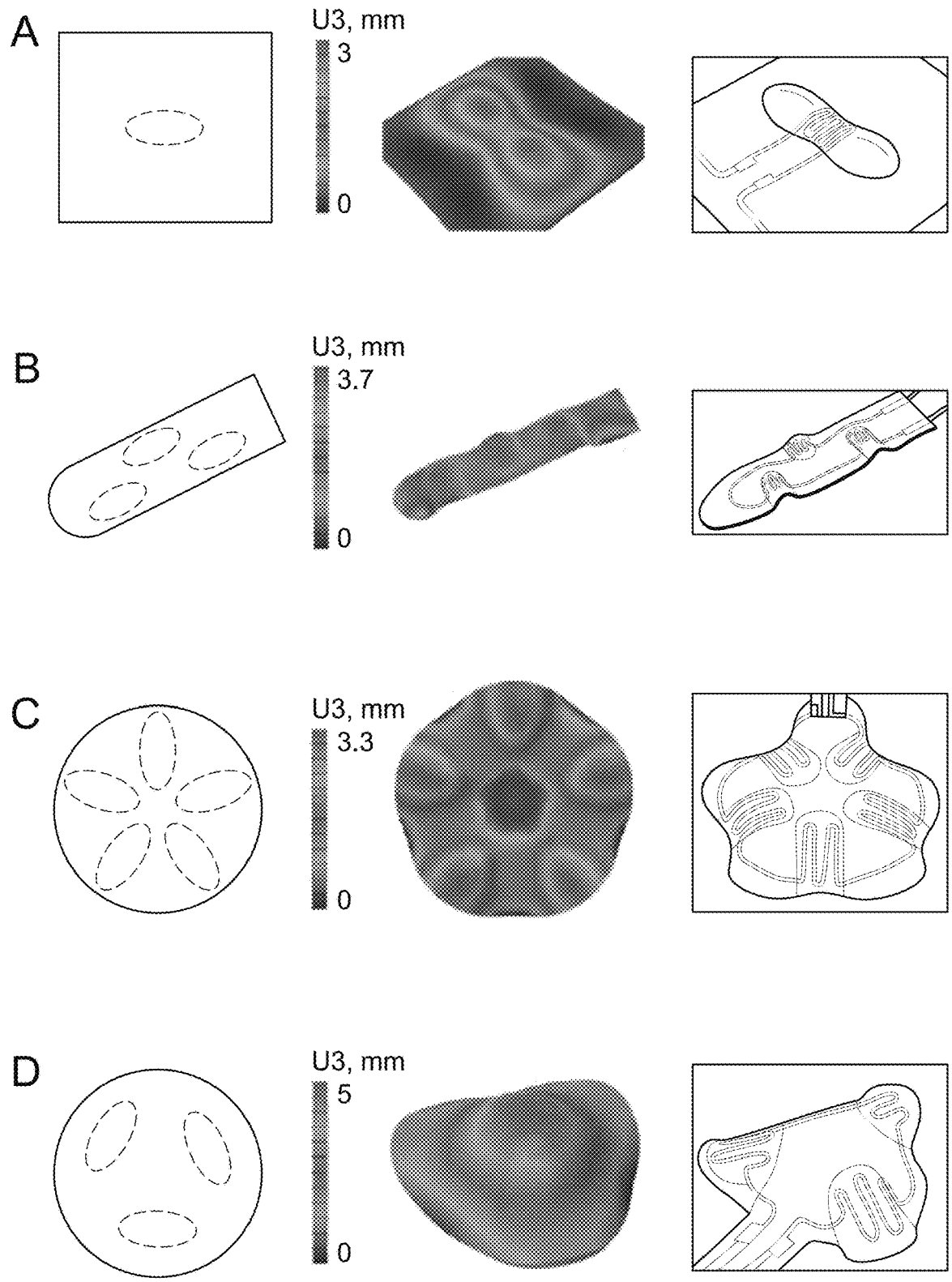
FIG. 8 illustrates a FEA simulation to predict different pattern changes (Panels (A)-(D)) for an LLAM, according to embodiments of the claimed invention.

To predict the deformation of certain designs under stimulation, a mechanical simulation was carried out as shown in FIG. 8. A UMAT was developed to simulate the shrinking behavior of the LCE materials, and the topologies under stimulation can be obtained in the simulation.

A steady sate thermal analysis of the LLAM was carried out to reveal the mechanism of bending, in the simulation the heater was set at a constant temperature of 110° C., which is measured from a thermal camera. The surface temperature distribution was first compared to the experimental results shown in FIG. 2C, left. Cross-section temperature distribution reveals the difference between layers. Combining the results in FIG. 7B, a strain mismatch of about 50% on each side leads to the bending of the actuator.

Figure 2:
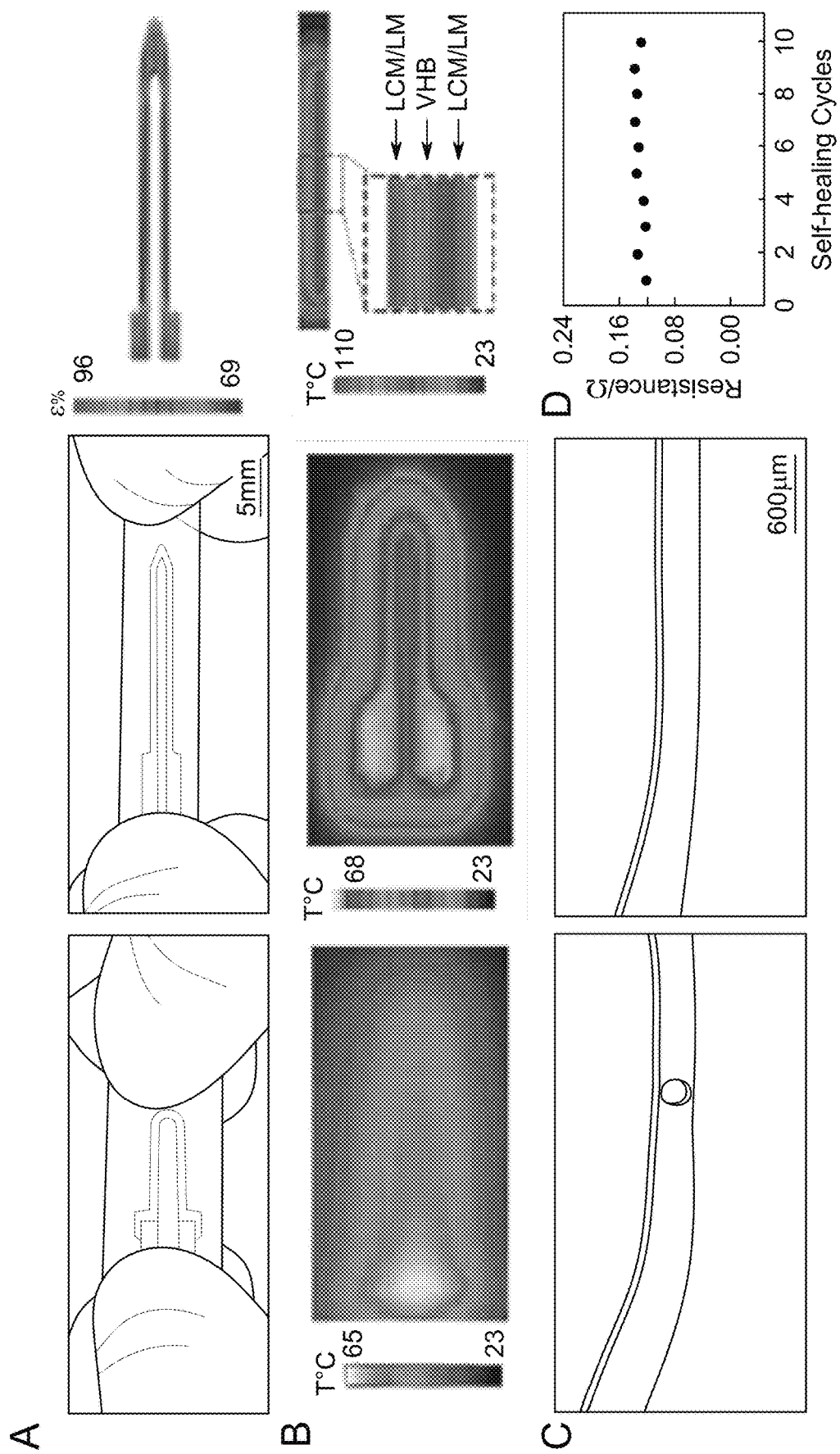
FIG. 2 depicts characterizations of an LLAM, according to embodiments of the claimed invention. Panel (A) depicts experimental images and finite element analysis (FEA) results illustrating the LM deforming along with the LCE substrate during a 2nd stage UV programming. The FEA results reveal strains larger than 69% while the LM remains conductive. Panel (B) illustrates thermal images of the surface of an LCE/LM actuator during a full actuation mode and cross-section temperature distribution of the actuator. The thermal image and cross-section temperature distribution explain how temperature varies inside of the actuator. The temperature distribution also explains why bending occurs when one side of the actuator is heated. Panel (C) illustrates self-healing characteristics of the LM channel encapsulated by LCE. After 10 cycles of damaging the LM and allowing for self-healing, the conductivity of the LM heater doesn't experience any increase or decrease. Panels (E-G) depict experimental tests, which illustrate the performance of the LCE actuator while bending, shrinking and twisting. A current of 3 A, 3.5 A, 4 A, 4.5 A, and 5 A were supplied for the actuation. Panels (H-J) illustrate cycle tests of the LCE/LM actuator for 100 cycles. As shown, the performances remain relatively the same.
Figure 2:
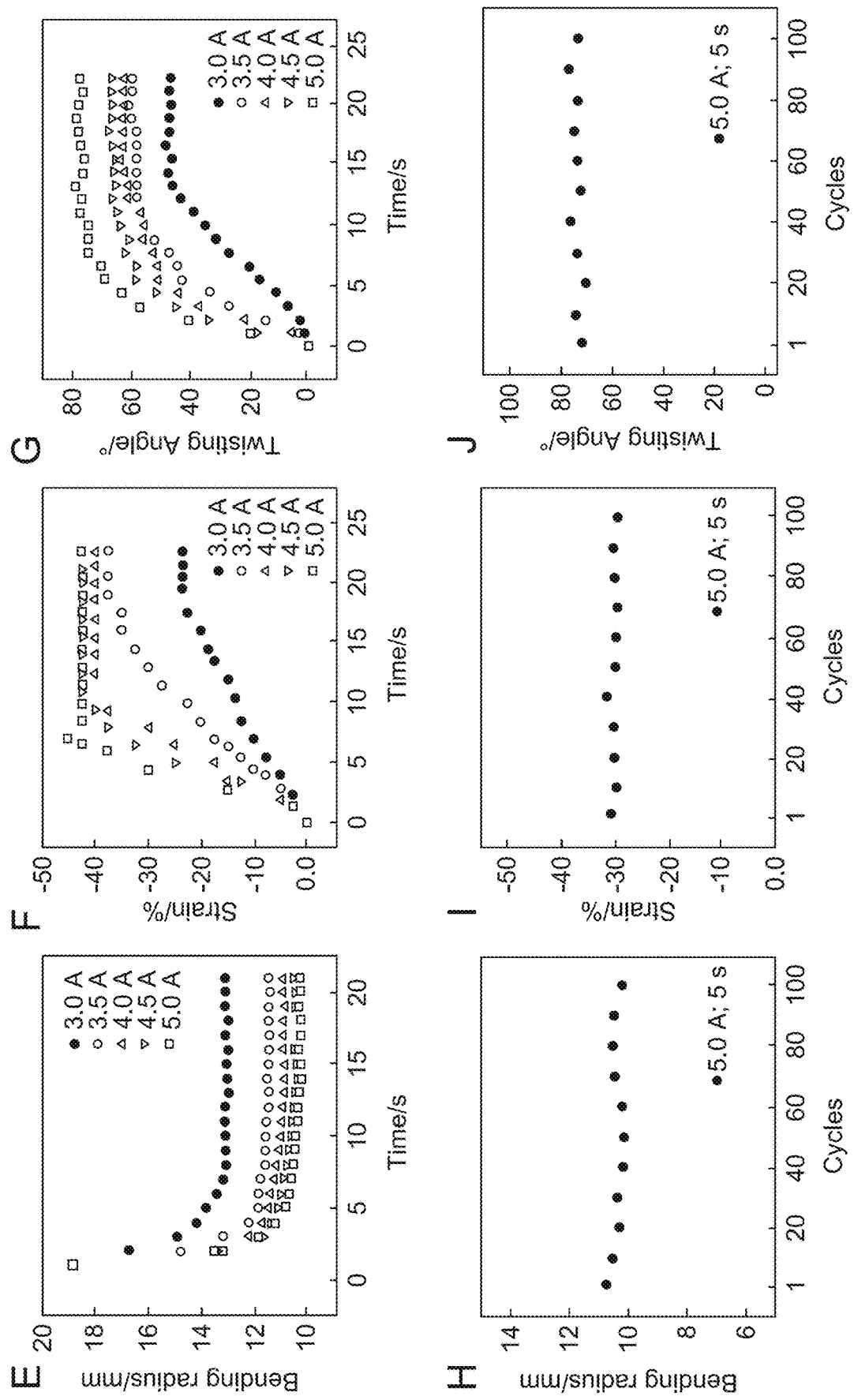

The thermal analysis for the LLAM in FIG. 2 was carried out based on steady state heat transfer analysis, which is due to the bending actuator holding its deformation at a steady state. While the one in FIG. 9F was based on transient heat transfer analysis, the robot only actuated for less than 8 s in the application. Noted here that during measurement, almost no resistance change of the LM sensor was observed, however, the temperature does rise according to the FEA analysis. This is mainly due to the low resistance of the LM sensor that our instruments could not catch an even smaller change.

The thermal conductivity of the PDMS, VHB, LCE, and LM used in the simulation are 0.15 W/(mK), 1.5 W/(mK), 0.2 W/(mK), and 29 W/(mK) respectively. In addition, Sink temperature of 25° C. was used.

Figure 9:
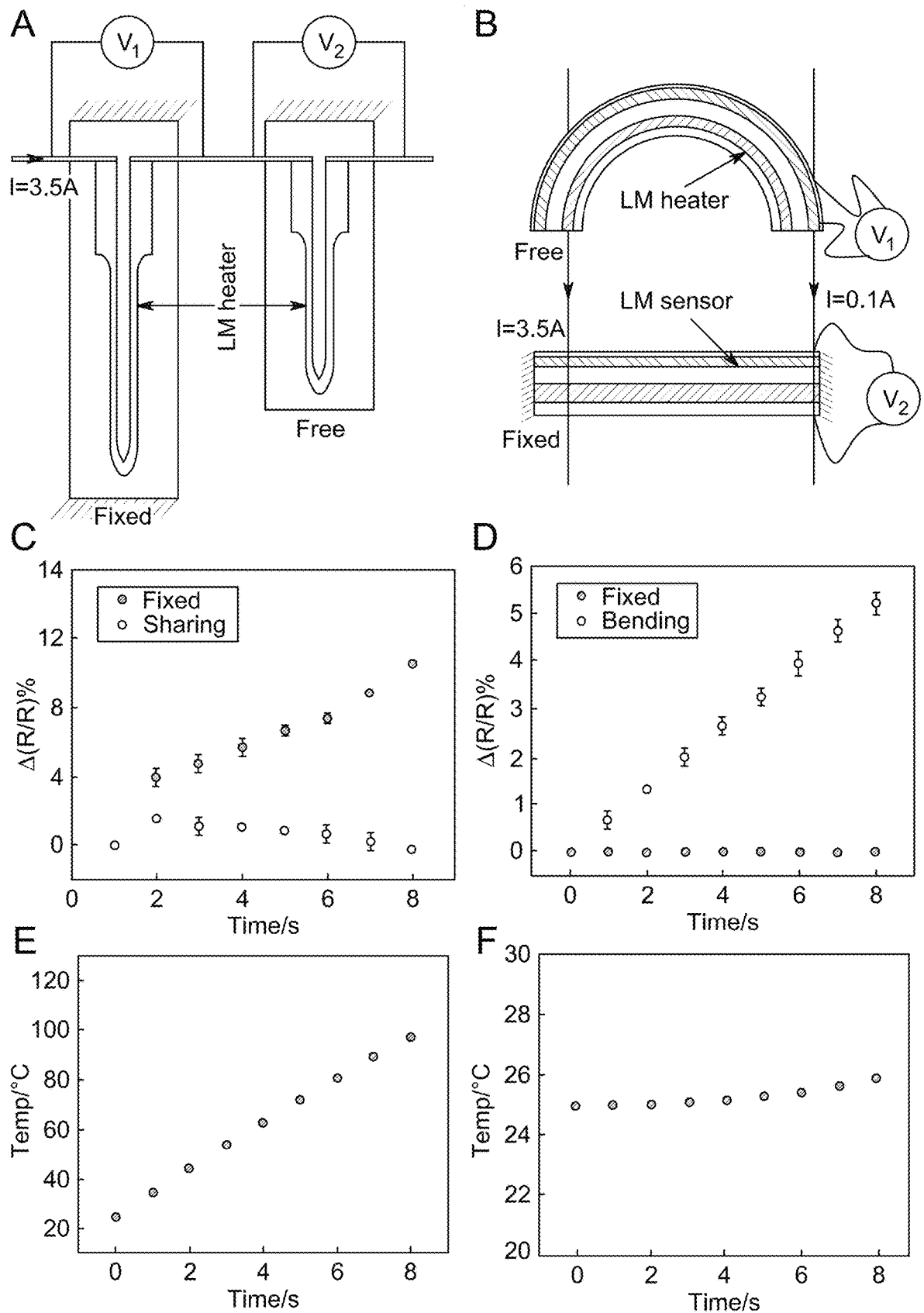
FIG. 9 depicts self-sensing characterizations of both LLAM and APAT, according to an embodiment of the claimed invention.

Self-Sensing Characterization of Both Linear LCE/LM Actuator and Bending LCE/PDMS/LM Actuator Both the bending self-sensible actuator and the linear shrinking actuators are studied for their self-sensibility. The linear actuator changed its resistance due to both deformation and heat, and the measured resistance change is coupled. A study about the resistance change during the actuation and a comparison experiment were also carried out as well as indicated in FIG. 9A. A current of 3.5 A was applied to two linear actuators fabricated with the same method and with the same size. One actuator was fixed at two ends while the other was allowed to deform freely on one end. A four point measurement method was adopted to measure the resistance change of both actuators and the results are shown in FIG. 9C. An overall negative resistance change was observed for the linear actuator. Transient heat transfer simulation shows the change of temperature of the LM heater before 8 s, indicated in FIG. 9E.

The bending actuator is based on a more complex design and was aimed at excluding the influence of the heat. The actuator was based on APAT design and two separated LM patterns were fabricated on each side, as described in the main text and shown in FIG. 9B. There is a layer of 2 mm PDMS in between which served as insulation material. A current of 3.5 A was applied to both the bottom heaters for 8 s and another testing current of 0.01 A was applied to the upper sensors. One of the actuators was fixed at two ends as a comparison experiment while the other was allowed to move freely. The resistance change of the upper LM sensors was recorded for 10 s and the results show very good insulating of the heat from deformation. FIG. 9D shows almost no change of resistance for the fixed case, while more obvious resistance change for the free-moving one. Further transient thermal analysis also reveals that the change of temperature of the LM sensor before 8 s is not obvious, as indicated in FIG. 9F.

Independent Controlling of LCE/Ecoflex/LM System

Figure 10:
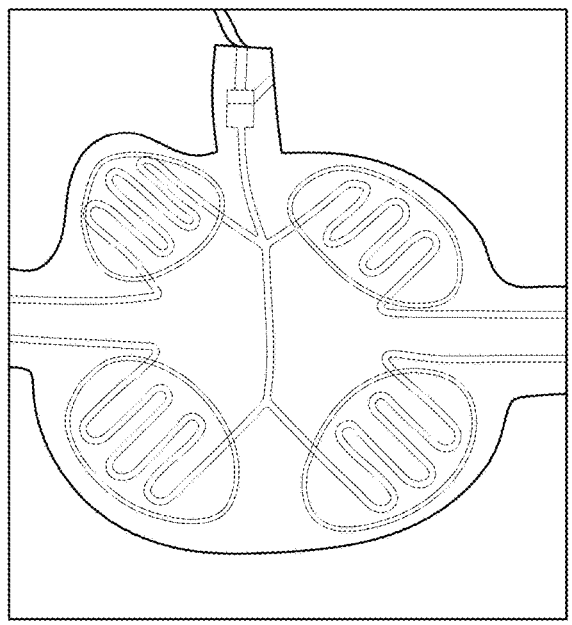
FIG. 10 depicts independent controlling of different actuation units for an APAT, according to embodiments of the claimed invention.
Figure 10:
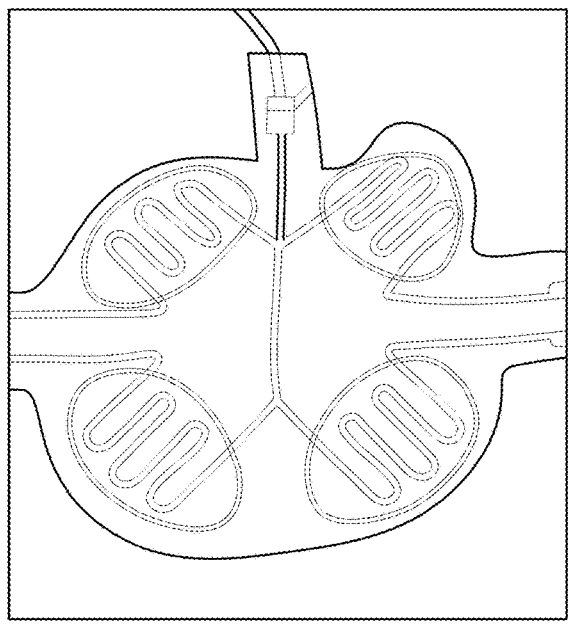
Figure 10:
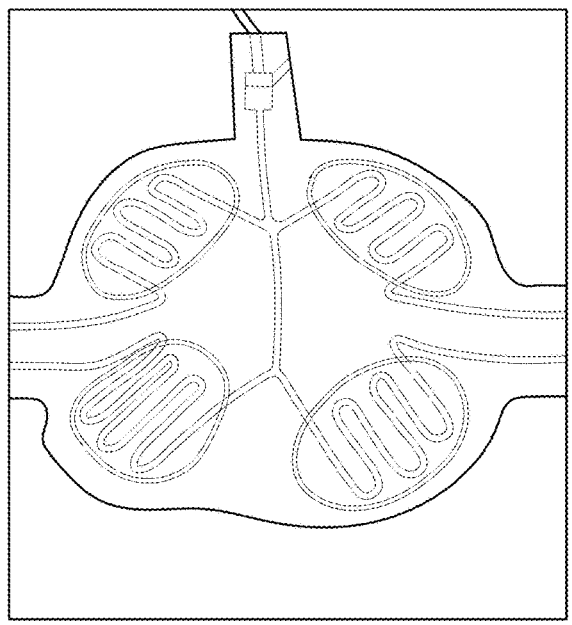
Figure 10:
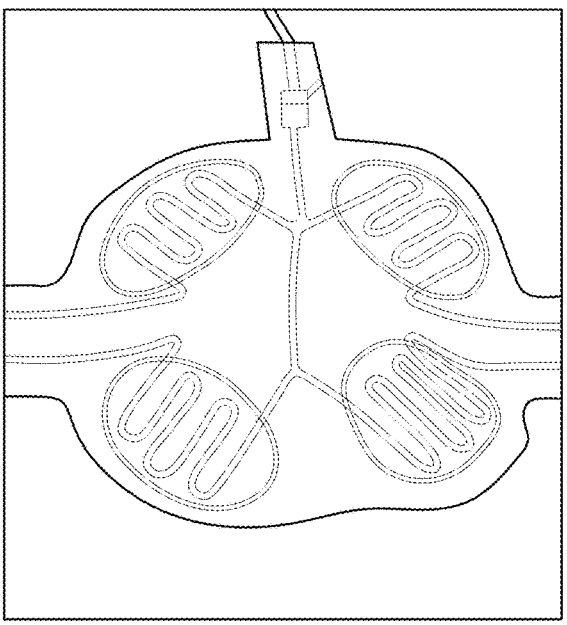

The APATs are made with different deformable units, and can thus be controlled independently, shown in FIG. 10. The heater patterns are designed in a way that currents can be applied independently, which can also be seen in FIG. 10. Four independent LCE elements were attached under each heaters and can be controlled to form four different patterns.

Uni-Friction Soft Walker Feet

Figure 11:
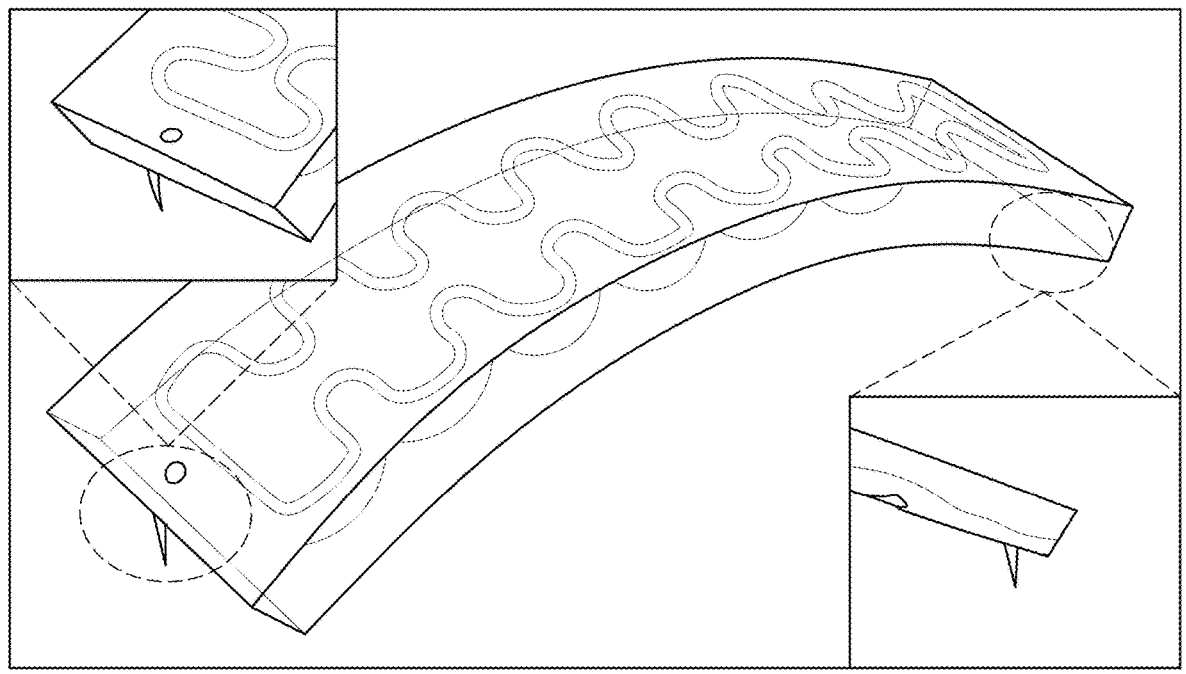
FIG. 11 depict uni-frictional 'feet' for the soft walker, according to an embodiment of the claimed invention.

The soft walker in FIG. 4 has three uni-friction feet, which helps the walker moving forward. The uni-friction feet were made with three needle hooks, all of which are facing backwards, as shown in FIG. 11. The feet enables the soft walker to move forward by front grabbing and rear pushing, during heating up and relaxing respectively.

Experimental Setup 2

As one of the most important prosthetic parts for disabled persons, commercialized prosthetic hands still facing a bulky, heavy and complex design. A light weight, flexible, and low cost prosthetic hand is in demand. However, one of the challenges is the "muscle" that drives the joints and parts, conventional options are step motors and complex transmissions, which lead to the heavy and bulky design. Smart materials that are soft, light and low cost offer better options for such application, for examples, shape memory Alloy and dielectric elastomers. In this paper, a new type of artificial muscle based on Liquid Crystal Elastomers has been incorporated into a prosthetic hand and achieved basic functionalities, as well as the corresponding characterizations.

Introduction

Prosthetic hands, as one of the most important parts serving disabled persons, have been devoted into huge efforts in the last few decades. However, most of the econometrical prosthetic hands still lack in durability, high performance, lightweight, Bionic-look, and affordability. Various designs have been adopted such as Vincent hand, ILimb, Bebionic hand, and Michelange hand. All those commercial prosthetic hands are based on a mechanical design that have stiff joints and low degrees of freedom, since all the power sources are from DC motors. This in turn leads to the bulky, heavy, complex and expensive products in the market nowadays. To overcome this, new mechanisms for actuators have been introduced. Instead of using DC motor and mechanical gear systems, a tendon driven design has been introduced and is able to mimic the natural movements of human hands. However, such designs are still depended on DC motor as the power and require more space for the interconnectors between artificial tendons and the motors.

The key solution to such problems lie in the power source for actuation. Integrating smart materials into such systems is thus promising. In other prosthetic parts, for example, a prosthetic arm equipped with a thermal pneumatic artificial muscle was successfully achieved. Other pneumatic powered health care and aid devices have been developed as well. Apart from these, shaped memory alloys are also good candidates and are easy fabricated. More recently, dielectric elastomers are also included in such systems and get good performance. Among those smart actuators, Liquid Crystal Elastomers (LCEs) attracted people's attention due to their actuating the most similar to natural muscles. Design and incorporation of such materials into a prosthetic hand could potentially enable the artificial part to function just like the real one. In this work, a novel prosthetic hand combining the most up-to-date technology of Liquid Crystal Elastomer has been demonstrated. Previous actuation methods for LCEs are subjected to a heating method, which can involve embedding a heater. However, those embedded heaters are either too rigid or too brittle. Here, we combined LCE actuators with LM heaters in a way that results in both large actuation strain and robustness. Firstly systematic fabrication and characterization methods were explained, and then a tendon-pulley finger structure was adopted for integrating the LCE muscle into the prosthetic hand. Demonstrations of gestures and grabbing objects were shown at the end.

RESULTS

Figure 12:
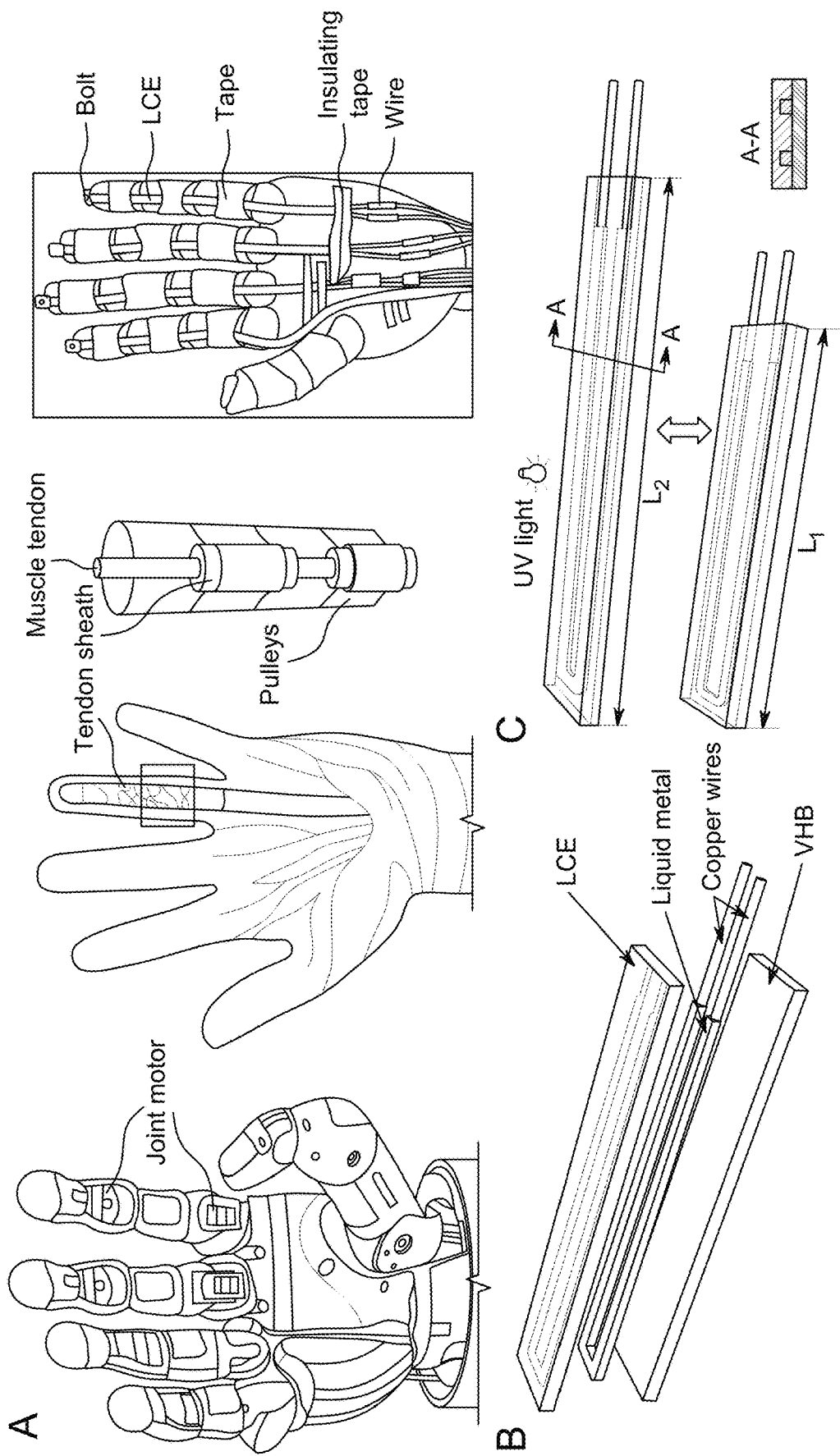
FIG. 12 illustrate designs, fabrication, and structure of LCE according to embodiments of the claimed invention. Panel (A) illustrates a robot hand actuated by a joint motors (left), the tissue structure of real fingers (middle) and the structure of a robot hand based on LCE actuation (right). Panel (B) depicts structure of LCE. Panel (C) illustrates the working principle of LCE programming and actuation.

The prosthetic hand in this work, in contrast to conventional motor-joint ones, is based on a bio-inspired design shown in FIG. 12A. The actuation materials are the tendons that are fixed onto the prosthetic hand, as indicated in FIG. 12A left. For each finger, there is a strip of "tendon" that consists of LCE and a LM heater, where three "pulleys" are responsible for holding the "tendon" close to the finger. Meanwhile, all parts including the prosthetic finger joins are treated with lubricant oil, and the "tendons" are free to move within the "pulleys", mimicking natural human fingers. The pulleys in this work, to simplify the design, are made of rigid silicone tapes. During actuation, they will prevent the LCE tendon from rupturing off the finger.

The LCE "tendons" are based on a novel artificial muscle from our previous work. The LM heaters are embedded into the LCE strip, as indicated in FIG. 12B. The LM heater was patterned on top of sticky VHB layer utilizing a screen printing method, while two copper wires, which are used as external interconnectors, were connected at the end of the LM heater, the simple contact between the LM and the copper provided robust and good electric conductivity. Further, Liquid LCE (before curing) was casted on top of the VHB bonding layer and LM heater pattern and was allowed to cure at 80 degrees C. for 12 h. The sandwiched structure was then pre-stretched from original length L1 to a programed length L2, indicated in FIG. 12C. UV light was used here for fixing the programed state. Upon heating, in our case a current was applied through the copper wires, the LCE/LM actuators shrunk to the original length L1, and returned to L2 when it was cooled down. Noted here that the thickness of the VHB layer in the current design is only about 25 um which is thinner than the total thickness of the LCE (thickness: 1 mm) and LM layer (thickness: 0.6 mm). Thus its mechanical effect to the actuation can be ignored.

Figure 13:
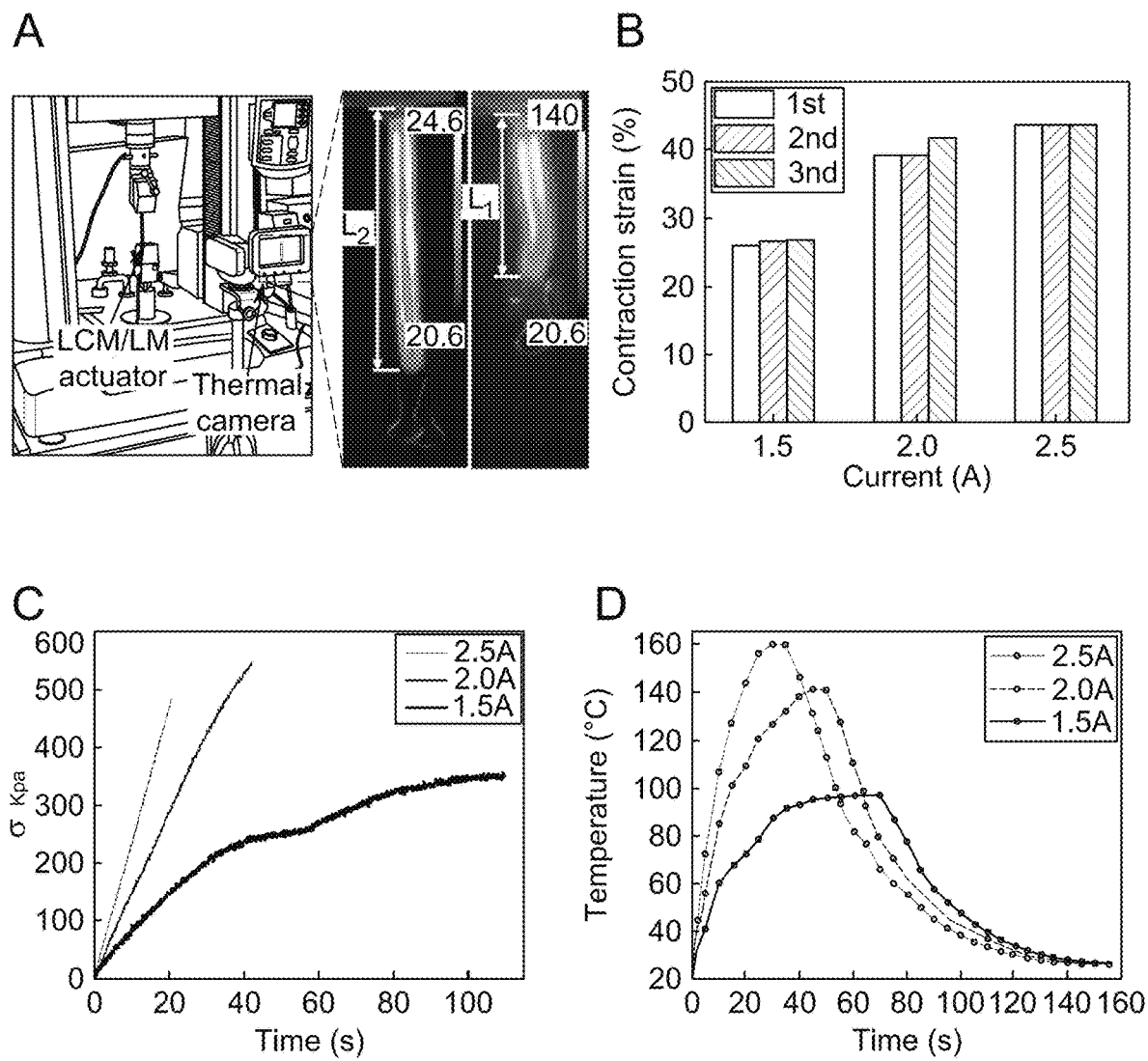
FIG. 13 illustrates the performance of LCE actuation, according to embodiments of the claimed invention. Panel (A) depicts an experimental set up for measuring the strain output of LCE muscle/tendon, (a thermal camera was used to detect both the strain and temperature (right)). Panel (B) illustrates the strain of LCE muscle at different current values, (3 samples are used here). Panel (C) depicts maximum stress output of LCE under different currents. Panel (D) depicts temperature change with respect to time under different current for LCE actuation.

To characterize the LCE/LM actuator, the sample was fixed at an Instron mechanical testing machine, and a thermal camera was placed nearby to record the temperature change as well as the actuation strain. A current generator was used for supplying constant and stable electric current through the LM heater, the joule heating eventually led to the phase transformation of the LCE, and deformation happened. In the first case, the LCE is fixed on the clamp with only one end, while keep the other end free standing, indicated in FIG. 13A. When current passed through the LM heater, the LCE shrunk freely from the programed length L1 to the original length L2, shown in FIG. 13A right. The thermal camera recorded both the actuation strain and temperature distribution on the surface of the LCE/LM actuator. Further, image analysis revealed the relationship between the strain and the current values. In the experiments, three current values are supplied: 1.5 A, 2 A, and 2.5 A respectively, and three times of testing were carried out for each current value, as indicated in FIG. 13B. The shrinking strain increases with an increase of current, due to an more overall higher temperature of the LCE network, which results in higher actuation strain.

A second characterization was carried out in case of two fixed ends on the mechanical testing machine, and the load was detected by the force sensor in the machine with respect to time. FIG. 13C shows the stress response of the LCE actuator after a constant 2 A current is applied. The results shows linear increase before 20 s, while it tends to reach a peak value at 50 s. Thus we notice that the maximum response time of the actuator and further cut the current at time of 50 s, both temperature and stress started to decrease at the same time. The total cooling time in this case was found out to be about 110 s, three times of testing was carried out as well, and the data of each test were close to each other (pattern-wise), as indicated in FIG. 13D.

Figure 14:
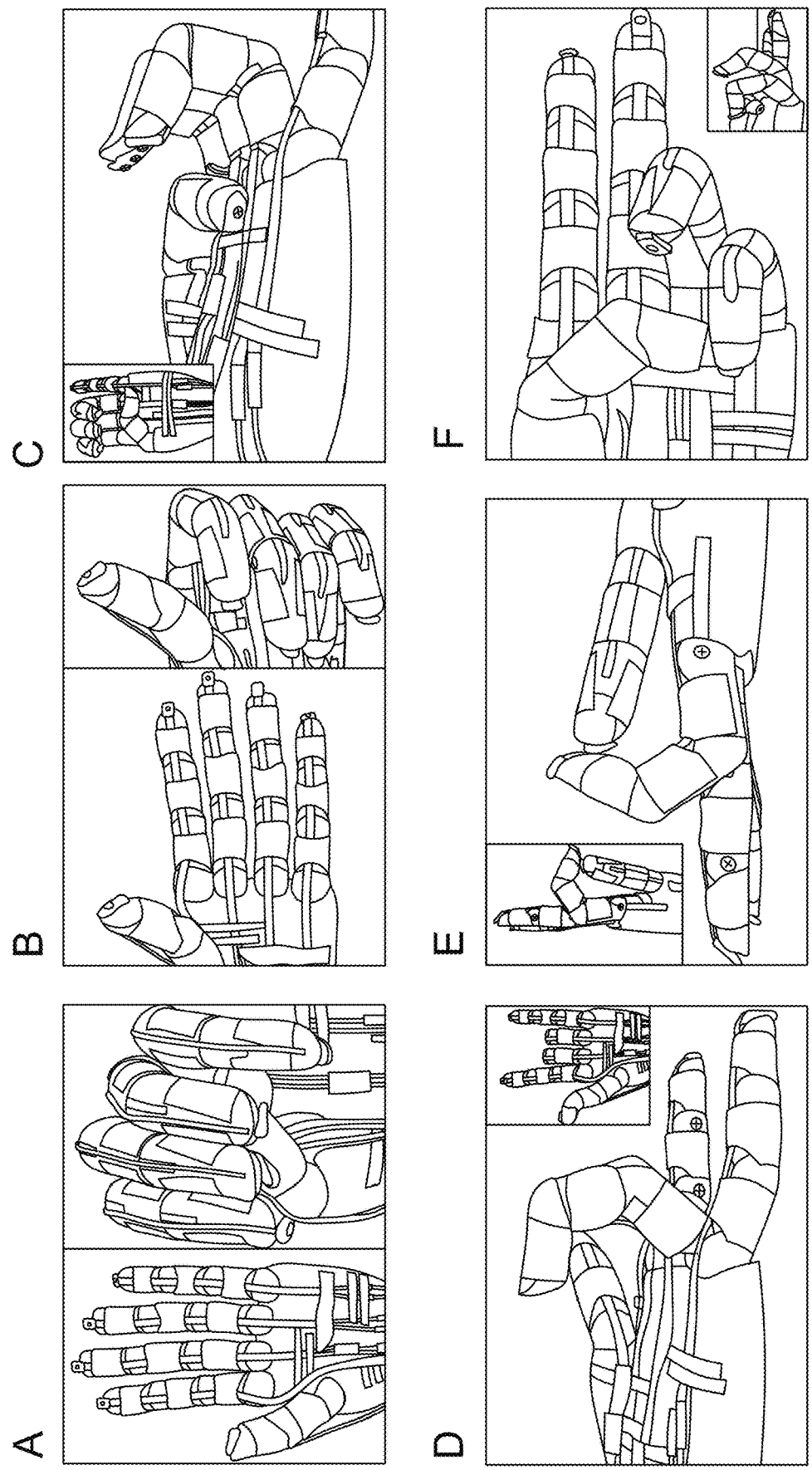
FIG. 14 illustrates the control of soft robotic fingers to achieve different actions, according to embodiments of the claimed invention. Panel (A) depicts the control of five fingers to bend at the same time in an upright position. Panel (B) depicts the control the index finger, middle finger, ring finger and little finger to bend at the same time in an upright position. Panel (C) depicts the control the thumb, forefinger, middle finger, and ring finger to bend at the same time. Panel (D) depicts the control the middle finger and the ring finger to bend at the same time. Panel (E) depicts the index finger bending to make an "OK" action. Panel (F) depicts the control the thumb, the index and the middle finger to bend at the same time.

One of the basic functions of a prosthetic hand is to make different gestures, which requires independent controlling of each finger. Here we embedded the LCE tendon into each finger, which was confined with three "pulleys" that we mentioned earlier, shown in FIG. 14. Rubber bands were used as "extensor tendons" for the recovery of the fingers to their original shape, see FIG. 14A right. Then current was applied to all five tendons to make a "fist" gesture (FIG. 14A). Moreover, other gestures can be easily realized by independently controlling the fingers, for example, a "thumbs up" gesture can be made by actuating all the rest of the four fingers (FIG. 14B), and more examples are shown from FIG. 14C to FIG. 14F.

Figure 15:
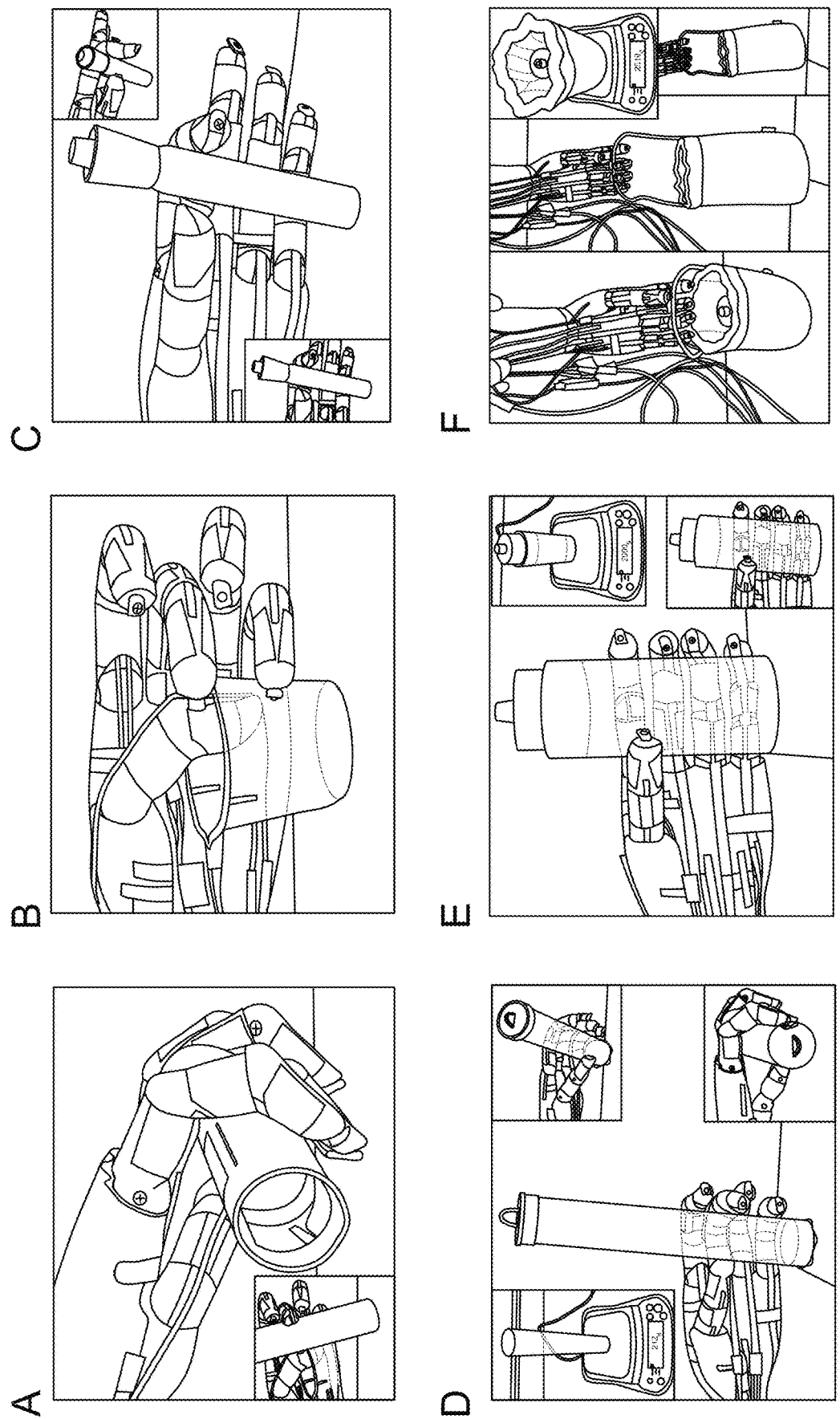
FIG. 15 illustrates the control of the soft robotic hand prosthetic to grab different objects, according to embodiments of the claimed invention. Panel (A) depicts the hand grabbing a paper tube. Panel (B) depicts the hand grabbing a cup. Panel (C) depicts the hand grabbing a pen. Panel (D) depicts the hand grabbing a slender plastic bucket which weighs 2.12 g. Panel (E) depicts the hand grabbing a bottle of water which weighs 200 g. Panel (F) depicts the hand lifting objects which weigh 251.9 g.

The prosthetic hand was able to perform more complex tasks like picking up or grabbing objects, shown in FIG. 15. Firstly, we demonstrated that the prosthetic hand is able to grab different shapes of objects, for example, a paper tube with diameter of 30 mm (FIG. 15A), a plastic beaker (FIG. 15B), and a marker pen (FIG. 15B). Those objects have different shapes and weight, while the prosthetic hand was able to handle all of them. Further, we tested the load carry capability of the prosthetic hand by letting it grabbing different weights of objects. The prosthetic hand can gently grab a light-weight soft plastic tube without breaking or deforming it (FIG. 15D, weight: 2.12 g), as well as firmly grab a water bottle with a total weight of 200 g. Only different current values were supplied to the LCE muscle for each case. Finally, a demonstration of lifting a bag with 251 g groceries was demonstrated in FIG. 15F.

Comments

In this work, a novel artificial muscle was introduced as the "tendon" of a prosthetic hand. The combination of LCE and LM was demonstrated in this work and their basic performance was characterized as well. The LCE/LM "tendons" has a robust behavior and large strain output. More promising formulas with a lower transition temperature may shorten the response. Meanwhile, our prosthetic hand is a solid wood piece which pertains a low thermal conductivity. Future design could focus on the shape and structure of a prosthetic hand that fits for the use of the LCE/LM actuators. Other functionalities like making gestures and lifting weight was demonstrated as well, and proved to be robust.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

What is claimed is:

1. A soft robotic actuator, comprising:
an elastomeric material defining a cavity;
a volume of liquid metal (LM) positioned within the cavity; and
an energy source coupled to the LM, wherein the energy source is adapted or configured to alter a temperature of the volume of LM, whereby altering the temperature of the volume of LM initiates an actuation of the elastomeric material,
wherein the cavity is further defined by a very high bonding (VHB) film coupled to the elastomeric material.

2. The soft robotic actuator of claim 1, wherein the altered temperature of the volume of LM causes a phase transition of the elastomeric material, wherein the actuation is initiated by the phase transition.

3. The soft robotic actuator of claim 1, wherein the actuation occurs according to a direction of alignment of the elastomeric material.

4. The soft robotic actuator of claim 1, wherein the actuation comprises a shrinking, a twisting, or a bending of the elastomeric material.

5. The soft robotic actuator of claim 1, wherein the volume of LM comprises Gallium, Caesium, Rubidium, Francium, Mercury, a Eutectic Gallium-based alloy, or a combination thereof.

6. The soft robotic actuator of claim 1, wherein the elastomeric material comprises liquid crystal elastomer (LCE), Polydimethylsiloxane (PDMS), a silicone rubber, or a combination thereof.

7. A soft robotic actuator, comprising:
an elastomeric material defining a cavity;
a temperature-activated pigment either painted onto or mixed into the elastomeric material
a volume of liquid metal (LM) positioned within the cavity; and
an energy source coupled to the LM,
wherein the energy source is adapted or configured to alter a temperature of the volume of LM, whereby altering the temperature of the volume of LM initiates an actuation of the elastomeric material.

8. A self-sensible soft robotic actuator comprising:
the soft robotic actuator according to claim 1;
another section of elastomeric material defining another cavity;
an LM sensor comprising another volume of LM positioned within the other cavity; and
a base layer comprising a first surface and a second surface, wherein the first surface is coupled to the soft robotic actuator and the second surface is coupled to both the other volume of LM and the other section of elastomeric material.

9. The self-sensible soft robotic actuator of claim 8, further comprising:
a data collector coupled to the LM sensor, wherein the data collector is adapted or configured to:
receive data corresponding to a change in resistance of the LM sensor;
determine, from the change in resistance, a change in strain on the LM sensor; and
identify from the change in strain on the LM sensor an actuation of the self-sensible soft robotic actuator.

10. A soft robotic prosthetic comprising:
at least one finger prosthetic having a length, a proximal end, and a distal end, wherein the at least one finger prosthetic comprises a flexible structure configured to bend radially along the length of the prosthetic finger;
the soft robotic actuator of claim 1, wherein the soft robotic actuator is positioned along the length of the at least one finger prosthetic;
a plurality of pulleys coupling the soft robotic actuator to the finger prosthetic, wherein the at least one finger prosthetic bends when an energy current is generated by the energy source; and a base coupled to the proximal end of the at least one finger prosthetic.

\* \* \* \* \*